(12) United States Patent
Peultier et al.

(10) Patent No.: US 12,274,430 B2
(45) Date of Patent: Apr. 15, 2025

(54) SURGICAL SYSTEM AND METHOD

(71) Applicant: Warsaw Orthopedic, Inc., Warsaw, IN (US)

(72) Inventors: Bertrand Peultier, Les Hopitaux Neufs (FR); Loic Josse, Palm Beach Garden, FL (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 389 days.

(21) Appl. No.: 17/606,011

(22) PCT Filed: Apr. 23, 2019

(86) PCT No.: PCT/US2019/028628
§ 371 (c)(1),
(2) Date: Oct. 22, 2021

(87) PCT Pub. No.: WO2020/219019
PCT Pub. Date: Oct. 29, 2020

(65) Prior Publication Data
US 2022/0192645 A1 Jun. 23, 2022

(51) Int. Cl.
*A61B 17/02* (2006.01)

(52) U.S. Cl.
CPC .... *A61B 17/025* (2013.01); *A61B 2017/0256* (2013.01)

(58) Field of Classification Search
CPC ... A61B 17/02; A61B 17/025; A61B 17/0206; A61B 17/0256; A61B 17/0293; A61B 17/70; A61B 17/7076; A61B 17/708; A61B 17/7077; A61F 2/44
See application file for complete search history.

(56) References Cited

U.S. PATENT DOCUMENTS

| | | |
|---|---|---|
| 6,030,402 A | 2/2000 | Thompson et al. |
| 6,139,493 A | 10/2000 | Koros et al. |
| 8,974,497 B2 | 3/2015 | Cho et al. |
| 9,402,660 B2 | 8/2016 | Brinkman et al. |
| 10,314,620 B2 | 6/2019 | Cho et al. |
| 2006/0084844 A1 | 4/2006 | Nehls |

(Continued)

FOREIGN PATENT DOCUMENTS

| | | |
|---|---|---|
| CN | 101489497 | 7/2009 |
| CN | 108498152 | 9/2018 |

(Continued)

OTHER PUBLICATIONS

International Search Report for PCT/US2019/028628 date of completion is Feb. 21, 2020 (2 pages).

(Continued)

*Primary Examiner* — Christopher J Beccia
(74) *Attorney, Agent, or Firm* — Sheridan Ross P.C.

(57) ABSTRACT

A surgical instrument includes a first member having a mating surface that is connectable with a first blade and a height controller. The height controller is connectable with a surgical distractor and configured to translate the first member relative to the surgical distractor. A second member includes a second blade and is movable relative to the first member such that the blades are movable to space tissue adjacent a spine. Surgical systems, constructs, implants and methods are disclosed.

20 Claims, 28 Drawing Sheets

(56) References Cited

U.S. PATENT DOCUMENTS

| | | |
|---|---|---|
| 2007/0208227 A1 | 9/2007 | Smith et al. |
| 2008/0140129 A1 | 6/2008 | Dalton |
| 2010/0069976 A1* | 3/2010 | de Villiers ............ A61F 2/4657 606/86 R |
| 2012/0296172 A1 | 11/2012 | Raven, III et al. |
| 2012/0316609 A1 | 12/2012 | Wall et al. |
| 2013/0310942 A1 | 11/2013 | Abdou |
| 2014/0024900 A1 | 1/2014 | Capote et al. |
| 2014/0066718 A1 | 3/2014 | Fiechter et al. |
| 2014/0107656 A1 | 4/2014 | Masson et al. |
| 2014/0257044 A1 | 9/2014 | Blain et al. |
| 2014/0257312 A1 | 9/2014 | Solitario, Jr. et al. |
| 2014/0350347 A1 | 11/2014 | Karpowicz et al. |
| 2015/0045834 A1 | 2/2015 | McBride |
| 2015/0164569 A1* | 6/2015 | Reitblat ............. A61B 17/7077 606/279 |
| 2015/0351738 A1 | 12/2015 | Perrow |
| 2016/0074029 A1 | 3/2016 | O'Connell et al. |
| 2016/0089188 A1 | 3/2016 | McBride, Jr. et al. |
| 2016/0206442 A1 | 7/2016 | Dvorak et al. |
| 2016/0345952 A1 | 12/2016 | Kucharzyk et al. |
| 2017/0035406 A1 | 2/2017 | Abidin et al. |
| 2017/0100116 A1 | 4/2017 | Erramilli et al. |
| 2017/0112539 A1* | 4/2017 | Hayes .................. A61B 17/708 |
| 2017/0119449 A1 | 5/2017 | Jones et al. |
| 2017/0215856 A1 | 8/2017 | Martinelli et al. |
| 2017/0252107 A1 | 9/2017 | Jones et al. |
| 2017/0258502 A1 | 9/2017 | Abdou |
| 2017/0311985 A1 | 11/2017 | Bobbitt et al. |
| 2018/0042594 A1 | 2/2018 | Miles et al. |
| 2018/0161101 A1 | 6/2018 | Barsoum et al. |
| 2018/0289363 A1 | 10/2018 | Barnes et al. |
| 2018/0303473 A1 | 10/2018 | Spann et al. |
| 2018/0303552 A1 | 10/2018 | Ryan et al. |
| 2019/0021716 A1 | 1/2019 | Waugh et al. |
| 2019/0046239 A1 | 2/2019 | Bobbitt et al. |
| 2019/0069956 A1 | 3/2019 | Ryan et al. |
| 2019/0090864 A1 | 3/2019 | Medeiros et al. |
| 2019/0090979 A1 | 3/2019 | Medeiros et al. |
| 2019/0110785 A1* | 4/2019 | Serokosz ........... A61B 17/0206 |
| 2019/0216453 A1 | 7/2019 | Predick et al. |
| 2019/0223854 A1 | 7/2019 | Baudouin et al. |
| 2020/0054361 A1 | 2/2020 | Peultier et al. |
| 2022/0192647 A1 | 6/2022 | Josse et al. |
| 2022/0202405 A1 | 6/2022 | Josse et al. |
| 2022/0202450 A1 | 6/2022 | Josse et al. |
| 2022/0218417 A1 | 7/2022 | Josse et al. |
| 2023/0059813 A1 | 2/2023 | Josse et al. |

FOREIGN PATENT DOCUMENTS

| | | |
|---|---|---|
| EP | 3331421 | 6/2018 |
| EP | 3351185 B1 | 7/2018 |
| GB | 2528416 | 1/2016 |
| KR | 101446620 B1 | 9/2009 |
| WO | WO 90/02527 | 3/1990 |
| WO | WO 2007/087536 | 8/2007 |
| WO | WO 2018/150214 | 8/2018 |
| WO | WO 2018/150215 | 8/2018 |
| WO | WO 2020/219016 | 10/2020 |
| WO | WO 2020/219018 | 10/2020 |
| WO | WO 2020/219019 | 10/2020 |
| WO | WO 2020/219020 | 10/2020 |
| WO | WO 2021/206723 | 10/2020 |

OTHER PUBLICATIONS

European Patent Office, 80298 Munich, Germany, Application No. 19925884.9, Extended European Search Report, dated: Aug. 11, 2022.

China Office Action: China National Intellectual Property Administration: Search Report: Application/Patent No. 201980095615.8:Jan. 23, 2024.

International Search Report and Written Opinion for International (PCT) Patent Application No. PCT/US2019/028615, dated Feb. 21, 2020, 8 pages.

International Preliminary Report on Patentability for International (PCT) Patent Application No. PCT/US2019/028615, dated Feb. 21, 2020, 7 pages.

Extended European Search Report for Europe Patent Application No. 19926119.9, dated Nov. 3, 2022, 9 pages.

Official Action for China Patent Application No. 201980095607.3, dated Jan. 25, 2024, 2 pages.

International Search Report and Written Opinion for International (PCT) Patent Application No. PCT/US2019/028624, dated Feb. 21, 2020, 9 pages.

International Preliminary Report on Patentability for International (PCT) Patent Application No. PCT/US2019/028624, dated Sep. 28, 2021, 7 pages.

Extended European Search Report for Europe Patent Application No. 19925802.1, dated Nov. 8, 2022, 10 pages.

Official Action for Europe Patent Application No. 19925802.1, dated Jul. 18, 2024, 3 pages.

International Preliminary Report on Patentability for International (PCT) Patent Application No. PCT/US2019/028628, dated Sep. 28, 2021, 6 pages.

International Search Report and Written Opinion for International (PCT) Patent Application No. PCT/US2020/027533, dated Jul. 6, 2020, 8 pages.

International Preliminary Report on Patentability for International (PCT) Patent Application No. PCT/US2020/027533, dated Oct. 6, 2022, 7 pages.

Extended European Search Report for Europe Patent Application No. 20930065.6, dated Mar. 13, 2024, 5 pages.

Official Action for U.S. Appl. No. 17/605,819, dated Feb. 15, 2024, 10 pages.

Official Action for U.S. Appl. No. 17/605,819, dated Jul. 22, 2024, 12 pages.

Official Action for U.S. Appl. No. 17/605,819, dated Sep. 27, 2024, 13 pages.

Official Action for U.S. Appl. No. 17/606,010, dated Dec. 20, 2023, 16 pages.

Notice of Allowance for U.S. Appl. No. 17/606,010, dated Jul. 9, 2024, 5 pages.

Corrected Notice of Allowance for U.S. Appl. No. 17/606,010, dated Jul. 29, 2024, 2 pages.

Notice of Allowance for U.S. Appl. No. 17/606,010, dated Sep. 16, 2024, 5 pages.

International Search Report and Written Opinion for International (PCT) Patent Application No. PCT/US2019/028612, dated Feb. 21, 2020, 7 pages.

International Preliminary Report on Patentability for International (PCT) Patent Application No. PCT/US2019/028612, dated Sep. 28, 2021, 6 pages.

Extended European Search Report for Europe Patent Application No. 19925665.2, dated Nov. 4, 2022, 10 pages.

International Search Report and Written Opinion for International (PCT) Patent Application No. PCT/US2019/028632, dated Feb. 21, 2020, 7 pages.

International Preliminary Report on Patentability for International (PCT) Patent Application No. PCT/US2019/028632, dated Sep. 28, 2021, 6 pages.

Extended European Search Report for Europe Patent Application No. 19925589.4, dated Nov. 7, 2022, 12 pages.

Official Action for China Patent Application No. 201980095623.2, dated Jan. 23, 2024, 2 pages.

Official Action for U.S. Appl. No. 17/606,013, dated Sep. 15, 2023, 5 pages. Restriction Requirement.

Official Action for U.S. Appl. No. 17/606,013, dated Mar. 21, 2024, 25 pages.

Official Action for U.S. Appl. No. 17/606,013, dated Jun. 12, 2024, 26 pages.

* cited by examiner

SURGICAL SYSTEM AND METHOD

CROSS-REFERENCE TO RELATED APPLICATIONS

This application is a National Stage Application of PCT/US2019/028628 filed Apr. 23, 2019, and the disclosure of the above-identified application is hereby incorporated by reference in its entirety.

TECHNICAL FIELD

The present disclosure generally relates to medical devices for the treatment of spinal disorders, and more particularly to a surgical system and a method for correction of a spinal disorder.

BACKGROUND

Spinal disorders such as degenerative disc disease, disc herniation, osteoporosis, spondylolisthesis, stenosis, scoliosis, kyphosis, and other curvature abnormalities, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, ligamentotaxy, corpectomy, discectomy, laminectomy, fusion, fixation and implantable prosthetics. Correction treatments used for positioning and alignment of vertebrae may employ spinal implants including spinal constructs and interbody devices for stabilization of a treated section of a spine. In some cases, the spinal implants may be manipulated with surgical instruments for compression and distraction of vertebrae. This disclosure describes an improvement over these prior technologies.

SUMMARY

In one embodiment, a surgical instrument is provided. The surgical instrument includes a first member having a mating surface that is connectable with a first blade and a height controller. The height controller is connectable with a surgical distractor and configured to translate the first member relative to the surgical distractor. A second member includes a second blade and is movable relative to the first member such that the blades are movable to space tissue adjacent a spine. In some embodiments, surgical systems, constructs, implants and methods are disclosed.

In one embodiment, a surgical system is provided. The surgical system includes a first implant support and a second implant support. The implant supports are engaged with bone fasteners fixed with vertebral tissue. A surgical distractor is engageable with the implant supports. A surgical retractor has a first member including a mating surface that is connectable with a first blade and a height controller part. The height controller is connectable with the surgical distractor and configured to translate the first member relative to the surgical distractor. The surgical retractor further has a second member including a second blade and is movable relative to the first member such that the blades are movable to space tissue adjacent a spine.

In one embodiment, the surgical system includes a first implant support and a second implant support. The implant supports are engaged with bone fasteners fixed with vertebral tissue. A surgical retractor is engageable with the implant supports and includes a first blade and a second blade. A stability element is disposed with the implant supports and alternately engageable with the first blade or the second blade.

BRIEF DESCRIPTION OF THE DRAWINGS

The present disclosure will become more readily apparent from the specific description accompanied by the following drawings, in which.

DETAILED DESCRIPTION

Figure 1:
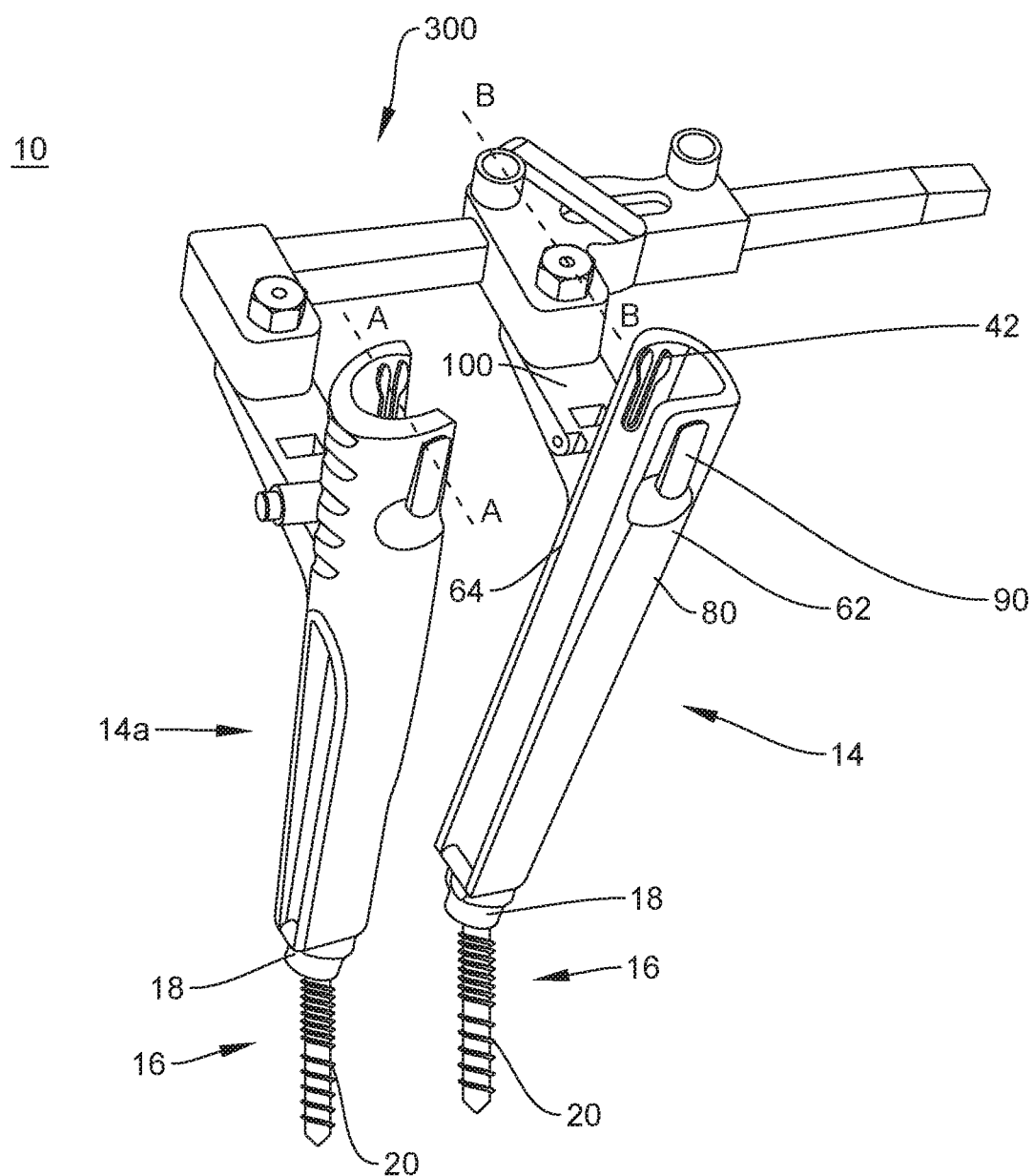
FIG. 1 is a perspective view of components of one embodiment of a surgical system in accordance with the principles of the present disclosure.

The exemplary embodiments of the system and related methods of use disclosed are discussed in terms of medical devices for the treatment of musculoskeletal disorders and more particularly, in terms of a surgical system and method for correction of a spine disorder. In some embodiments, the present surgical system includes surgical instruments that allow vertebral manipulation to treat spinal disorders, as described herein, for managing lordosis and/or kyphosis restoration. In some embodiments, the surgical instruments allow for parallel distraction and/or compression of vertebral tissue.

In some embodiments, the present surgical system includes a surgical trauma instrument. In some embodiments, the present surgical system is utilized with a method to correct complex spinal deformities. In some embodiments, the present surgical system is utilized with a method to treat degenerative spinal disorders and/or employed with transforaminal lumbar interbody fusion procedures. In some embodiments, the present surgical system is configured for utilization with a sagittal adjusting screw (SAS), a fixed axis screw (FAS) and/or a multi-axial screw (MAS). In some embodiments, the present surgical system comprises a single distractor to treat degenerative spinal disorders, for example, for disposal along a side of vertebrae oriented for decompression and/or interbody cage insertion.

In some embodiments, the present surgical system includes a surgical instrument connected with an adaptor, which is utilized with a bone screw having extender tabs attached thereto. In some embodiments, the present surgical system includes an implant support including a connector and an adaptor. In some embodiments, the connector includes an outer sleeve configured for connection with extenders. In some embodiments, the connector is connected with extenders for insertion of an implant, such as for example, a spinal rod. In some embodiments, the adaptor includes an arm having a pivot hinge that connects the connector with a compressor/retractor. In some embodiments, the pivot hinge allows movement of the components to provide surgical-site visibility for inter-operative imaging. In some embodiments, a compressor/distractor is utilized for generally parallel distraction. In some embodiments, a compressor/distractor is utilized for generally parallel compression. In some embodiments, the surgical instrument includes a compressor/distractor having a reversible ratchet with a neutral, freely movable position. In some embodiments, the present surgical system is employed with a procedure for implantation of a bone fastener percutaneously.

In some embodiments, the present surgical system includes a surgical instrument employed with a surgical method including the step of: pre-assembly of the distractor; pre-loading of the alignment guides; preparing for implantation of screws; connecting screw tabs; removal of the alignment guides; attaching a compressor/retractor having an articulating rack for segmental distraction; implanting an interbody and decompressing tissue, inserting a rod length caliper; inserting the rod and setscrews; performing segmental compression; breaking of setscrew tabs; and removing the compressor/distractor.

In some embodiments, the present surgical system includes an adaptor being employed with a surgical method including the step of inserting the implant support with a surgical site and the step of sliding a sleeve along the extender. In some embodiments, the method includes the step of securing the connector to the extenders. In some embodiments, the method includes the step of connecting a compressor/distractor with the implant support. In some embodiments, the method includes the step of actuating a rack and pinion mechanism disposed with the compressor/distractor to facilitate distraction or compression.

In some embodiments, the present surgical system includes a retractor provided to maintain the tissue in a medial-lateral orientation creating a channel for accessing the spine anatomy. In some embodiments, the retractor includes a first member including a mating surface being alternately connectable with a first blade and a part. The part is connectable with the compressor/distractor and configured to translate the first member relative to the compressor/distractor. The part is configured to translate the first member a height relative to the compressor/distractor. In some embodiments, the height is adjustable in a range between about 0 mm to about 50 mm. In some embodiments, the part is connected with the compressor/distractor by a dove tail projection disposed with the compressor/distractor. The dove tail projection facilitates a friction fit between the part and the compressor/distractor to fix the position of the part and/or the first member relative to the compressor/distractor. The retractor includes a second member connectable with a second blade. The second member is movable relative to the first member such that the blades are movable to space tissue adjacent a spine.

In some embodiments, the present surgical system includes a stability element configured for disposal with the implant supports and alternately engageable with the first blade or the second blade. In some embodiments, the implant supports include rod slots configured for slidable translation of the stability element. In some embodiments, the stability element includes at least one mating pin being alternately engageable with the first blade or the second blade. In some embodiments, the retractor is provided to maintain the tissue in a medial-lateral orientation creating a channel for accessing the spine anatomy. In some embodiments, the stability element is utilized to widen the channel in a medial and/or lateral direction.

In some embodiments, the present surgical system is employed with a surgical technique for the implantation of spinal implants, such as, for example, spinal rods and setscrews. In some embodiments, the spinal rods and setscrews are implanted percutaneously. In some embodiments, the spinal rods are reduced relative to a screw head. In some embodiments, the present surgical system is employed with a surgical technique for release of pressure applied during spinal rod reduction.

In some embodiments, the present surgical system includes a surgical instrument configured to compress or distract and restore curvature of a spine. In some embodiments, the present surgical system includes instruments and tools for correcting a sagittal deformity and rebalancing a spine of a body. In some embodiments, the present surgical system is employed to treat degenerative deformities of a spine in a sagittal plane, for example, degenerative kyphosis. In some embodiments, the present surgical system is employed to treat hyper-kyphosis, flat lumbar back, including disorders that create an unbalance of a body and loss of alignment between body parts. In some embodiments, the present surgical system provides a selected amount of correction to apply a selected balance to a spine and provides control and adjustment to the amount of correction. In some embodiments, the present surgical system includes a series of tools and instruments that allow formulation of a type of correction applied and can control the correction stabilization using posterior instrumentation.

In some embodiments, one or all of the components of the surgical system are disposable, peel-pack, pre-packed sterile devices used with a spinal construct. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis, kyphosis and other curvature abnormalities, tumor and fractures. In some embodiments, the present disclosure may be employed with other osteal and bone-related applications, including those associated with diagnostics and therapeutics. In some embodiments, the disclosed surgical system and methods may be alternatively employed in a surgical treatment with a patient in a prone or supine position, and/or employ various surgical approaches to the spine, including posterior and/or posterior mid-line and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternative embodiments are disclosed. Reference is made to the exemplary embodiments of the present disclosure, which are illustrated in the accompanying figures. Turning to FIGS. 1-10, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of surgical system 10 are configured for engagement with spinal constructs attached with vertebrae to manipulate tissue and/or correct a spinal disorder, such as, for example, a sagittal deformity, as described herein. In some embodiments, surgical system 10 may be employed with surgical procedures, such as, for example, corpectomy, discectomy and/or fracture/trauma treatment and may include fusion and/or fixation that employ implants to restore the mechanical support function of vertebrae.

Surgical system 10 includes a surgical instrument, such as, for example, an implant support 14 and an implant support 14a, similar to implant support 14, as described herein. Implant supports 14, 14a are connectable with a spinal implant, such as, for example, a bone fastener 16. Bone fastener 16 includes a receiver 18 and a screw shaft 20, as shown in FIG. 1. Screw shaft 20 is fixed with patient tissue in use of fastener 16. Each receiver 18 is connectable with one of implant supports 14, 14a to releasably engage a surgical instrument, such as, for example, a compressor/distractor 300 to distract and/or compress tissue.

Figure 2:
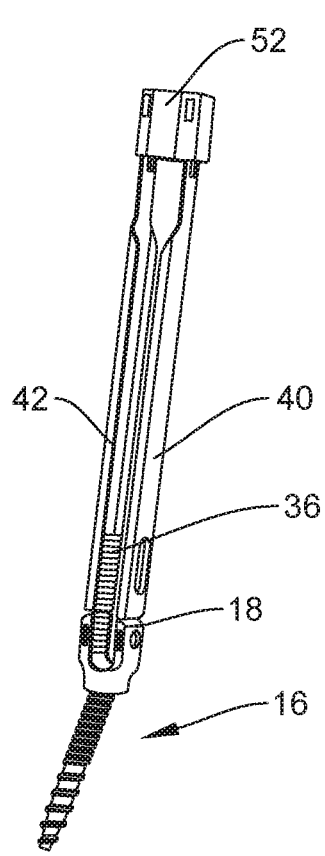
FIG. 2 is a perspective view of components of one embodiment of a surgical system in accordance with the principles of the present disclosure.
Figure 3:
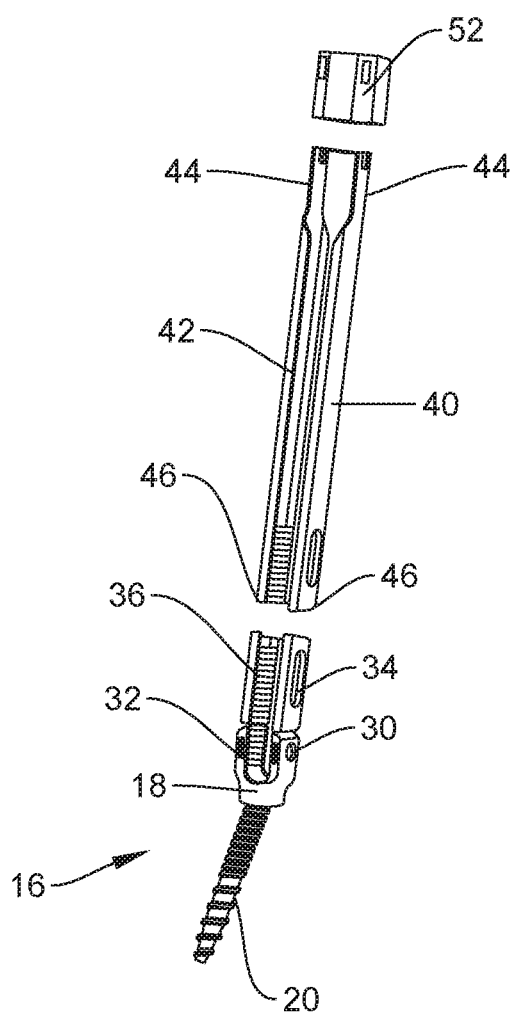
FIG. 3 is a perspective view of the components shown in FIG. 2 with parts separated.
Figure 24:
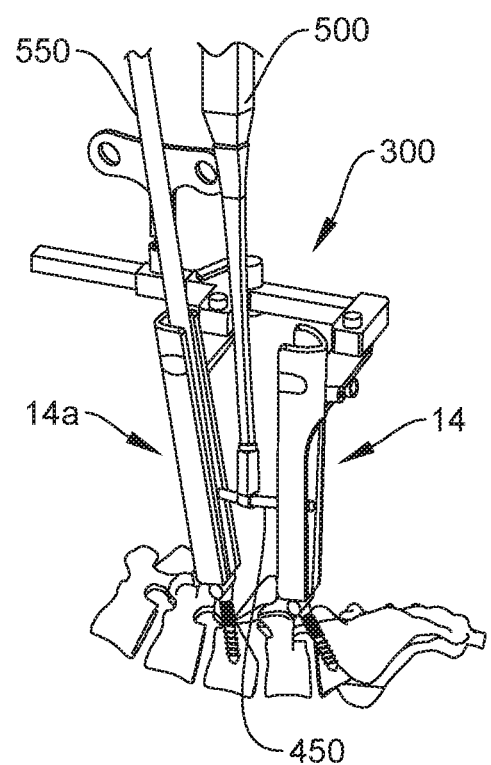
FIG. 24 is a perspective view of components of one embodiment of a surgical system disposed with vertebrae in accordance with the principles of the present disclosure.

Each receiver 18 includes a pair of spaced-apart arms 30, 32 (FIG. 3) that define an implant cavity configured for disposal of a component of a spinal construct, such as, for example, a spinal rod 450 (e.g., FIG. 24). Each receiver 18 includes an inner surface having a thread form, as shown in FIGS. 2 and 3. Bone fastener 16 includes screw shaft 20 configured to penetrate tissue, such as, for example, bone.

Arm 30 includes or is connected to a break-away tab 34 that is frangibly connected to arm 30, as shown in FIG. 2, such that manipulation of tab 34 relative to arm 30 can fracture and separate tab 34 from arm 30 at a predetermined force and/or torque limit. Arm 32 similarly includes or is connected to a break-away tab 36 that is frangibly connected to arm 32 such that manipulation of tab 36 relative to arm 32 can fracture and separate tab 36 from arm 32 at a predetermined force and/or torque limit. In some embodiments, as force and/or torque is applied to tabs 34, 36 and resistance increases, for example, the predetermined torque and force limit is approached allowing tabs 34, 36 to break off from arms 30, 32.

In some embodiments, each implant support 14, 14a includes extender tabs 40, 42 that are connectable with tabs 34, 36 and/or bone fastener 16. Each extender tab 40, 42 extends between a proximal end 44 and a distal end 46. Distal ends 46 are configured for slidable disposal of a portion of bone fastener 16, such as, for example, tabs 34, 36. In some embodiments, tabs 34, 36 are configured to releasably fix extender tabs 40, 42 to bone fastener 16 for connecting extender tabs 40, 42 to implant support 14, as described herein.

In some embodiments, an extender cap 52 is disposed with extender tabs 40, 42. Cap 60 is configured to align extenders tabs 40, 42 to resist and/or prevent splaying of extender tabs 40, 42. Cap 60 is configured as a guide to facilitate positioning of surgical instruments.

Figure 4:
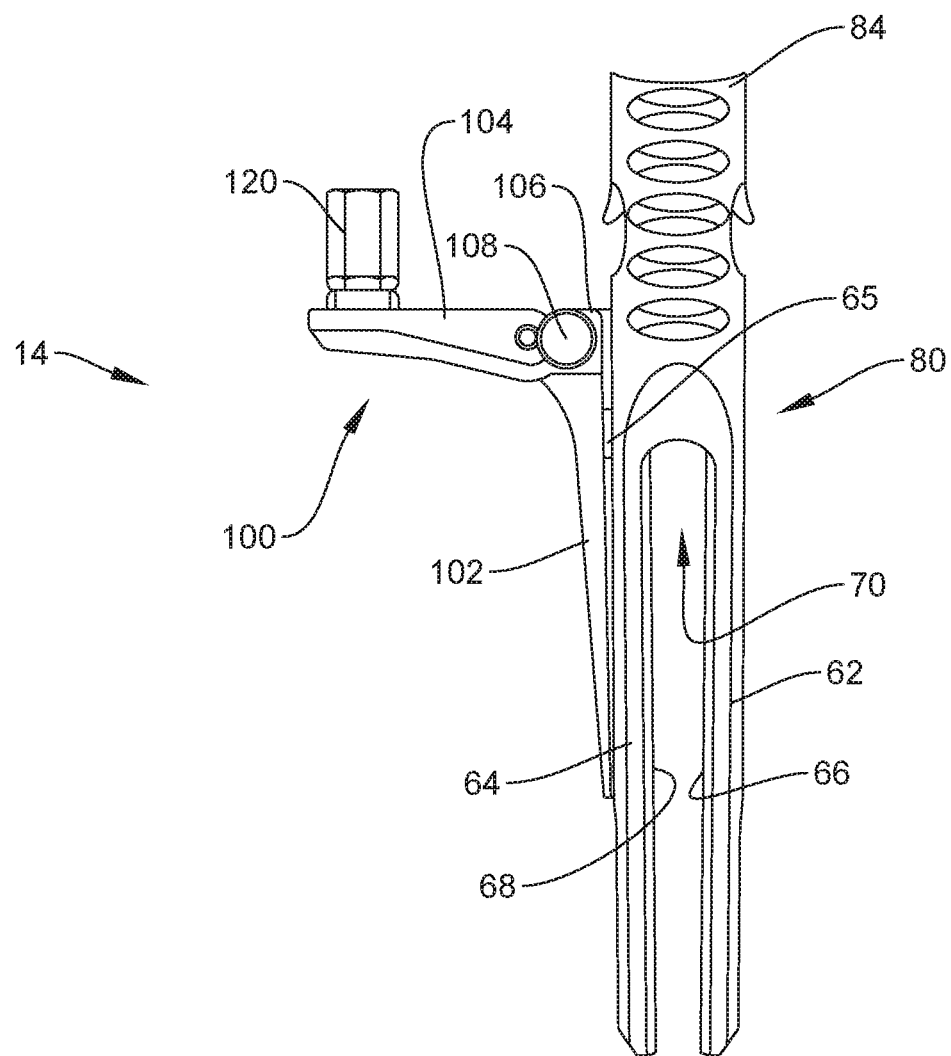
FIG. 4 is a break-away side view of components of one embodiment of a surgical system in accordance with the principles of the present disclosure.
Figure 5:
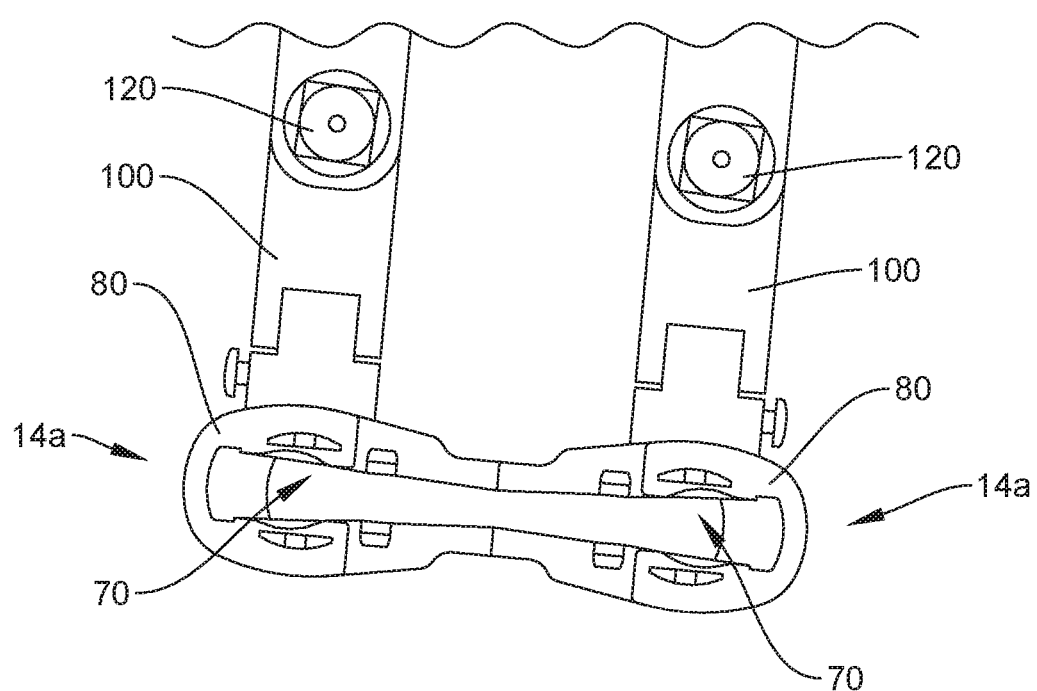
FIG. 5 is a top view of components of one embodiment of a surgical system in accordance with the principles of the present disclosure.

Implant support 14 includes a connector 80 to facilitate engagement of implant support 14 with extender tabs 40, 42. Connector 80 includes elongate members, such as, for example, sleeves 62, 64, as shown in FIGS. 4 and 5. Sleeve 62 includes a surface 66 and sleeve 64 includes a surface 68. Sleeves 62, 64 are configured for translation over extender tabs 40, 42. Sleeves 62, 64 are disposed in spaced apart relation and define a slot 70 configured for disposal of an implant, such as, for example, a spinal rod 450 (see e.g., FIG. 24).

Figure 6:
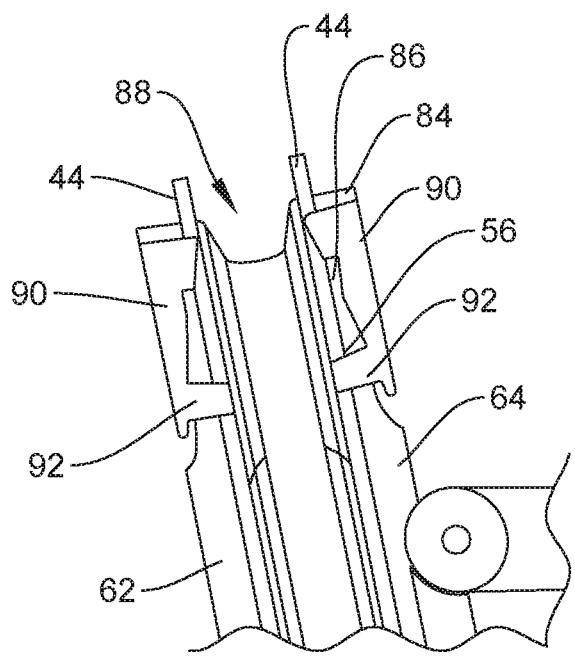
FIG. 6 is a cross section of components, taken along the line A-A in FIG. 1.

Connector 80 includes a wall 84. As shown in FIG. 6, wall 84 includes an inner surface 86 that defines a cavity, such as, for example, a pocket surface 88. Pocket surface 88 is configured for disposal of proximal ends 44 of extender tabs 40, 42, as also shown in FIG. 6. Pocket surface 88 is configured to resist and/or prevent disengagement of connector 80 from extender tabs 40, 42. In various embodiments, connector 80 includes a lock, such as, for example, a depressible button 90 configured for disposal between a lock, or locking, orientation and a non-locking orientation. In the lock orientation, button 90 releasably fixes implant support 14 with extender tabs 40, 42. In the non-locking orientation, implant support 14 is translatable relative to extender tabs 40, 42 for engagement and disengagement with bone fastener 16. Button 90 may be spring biased to a locked position, such as by a projection 92 defined by button 90 being biased in the lock orientation into engagement with a groove 56 to releasably fix implant support 14 with extender tabs 40, 42. In some embodiments, connector 80 includes one or a plurality of buttons 90.

Implant support 14 includes an adaptor 100 extending from connector 80, as shown in FIGS. 4 and 5. Adaptor 100 includes an extension 102 that extends along sleeve 64. Extension 102 is pivotally connected to sleeve 64 such that extension 102 can be rotated and/or angled, as described herein. In some embodiments, sleeve 64 includes a stopping element, such as, for example, a reinforcement rib 65 configured to resist and/or prevent rotation of extension 102 relative to sleeve 64. In some embodiments, the reinforcement element provides for an increased rigidity of implant support 14. In some embodiments, the reinforcement element resists and/or prevents inward rotation of extension 102. In some embodiments, the reinforcement element provides a reverse angle geometry to facilitate stability of extension 102.

Adaptor 100 includes an extension 104 rotatably attached with extension 102 such that extension 104 is rotatable relative to connector 80. Extension 104 extends transverse to extension 102. In some embodiments, extension 104 may be variously oriented relative to extension 102, such as, for example, perpendicular, angular and/or offset.

Extension 104 is connected with extension 102 by a pin hinge 106. Pin hinge 106 facilitates rotation of extension 104 relative to extension 102 and/or bone fastener 16. Extension 104 is rotatable through and angular range of about 0 degrees through about +/−90 degrees. In some embodiments, extension 104 includes a lock 108 configured to fix extension 104 in a selected orientation relative to extension 102 and connector 80. Lock 108 is disposable in a lock orientation and a non-locking orientation to facilitate selective orientation of extension 104. Rotation of extension 104 facilitates connection of implant support 14 to compressor/distractor 300 by providing for manipulation of implant support 14 into alignment with compressor/distractor 300, as described herein.

Figure 7:
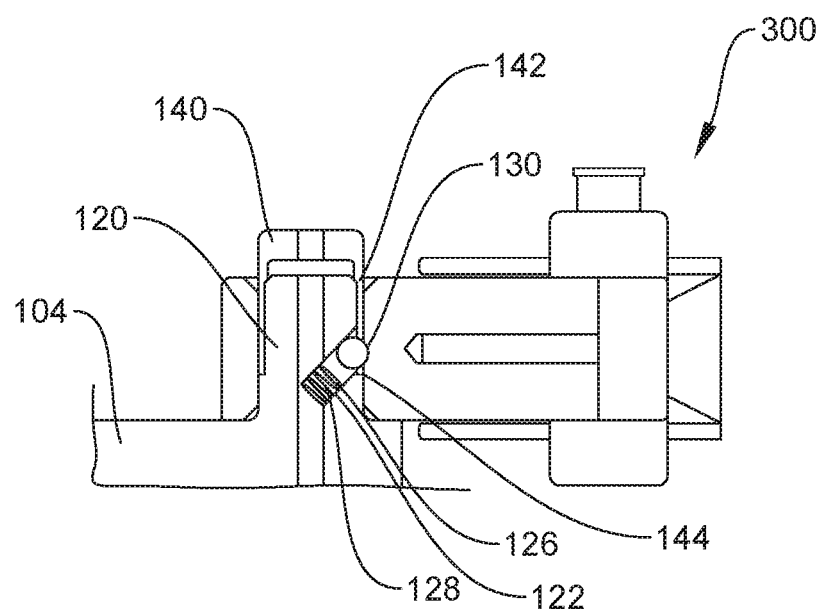
FIG. 7 is a cross section view of the components, taken along the line B-B in FIG. 1.

In various embodiments, extension 104 includes a protrusion 120 engageable with compressor/distractor 300 to releasably fix implant support 14 with compressor/distractor 300. Protrusion 120 includes a surface 122 that defines a transverse groove 126, as shown in FIG. 7. Protrusion 120 includes a lock, such as, for example, a spring-biased ball 130 that is configured for translation (and possibly also for some rotation) within groove 126 between a lock orientation and a non-locking orientation. A spring 128 disposed with groove 126 biases ball 130 toward the lock orientation.

Protrusion 120 is connectable with compressor/distractor 300. Compressor/distractor 300 includes a portion, such as, for example, a depressible button 140 configured for engagement with protrusion 120. Button 140 includes a wall 142 that extends circumferentially about protrusion 120 upon connection of compressor/distractor 300 to implant support 14. Wall 142 includes an end surface 144 that is engageable to ball 130 to translate ball 130 between the lock orientation and the non-locking orientation.

Figure 8:
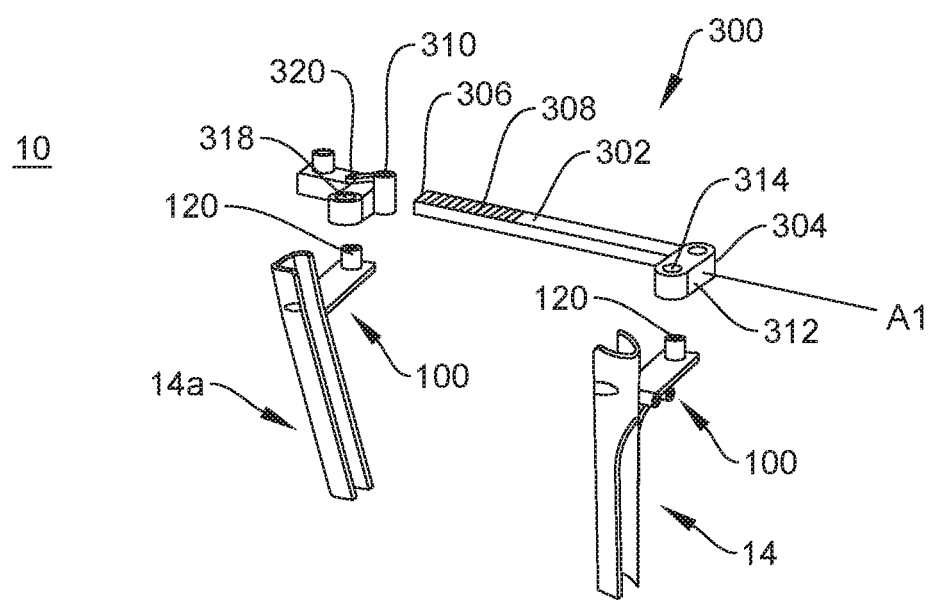
FIG. 8 is a perspective view of components of one embodiment of a surgical system in accordance with the principles of the present disclosure disposed with parts separated.

Compressor/distractor 300 includes a longitudinal element, such as, for example, a rack 302, as shown in FIG. 8. Rack 302 extends between an end 304 and an end 306 defining a longitudinal axis Al. Rack 302 is configured to connect adjacent implant supports 14, 14a to each other, as shown in FIG. 1. Rack 302 includes an outer surface having a plurality of teeth, such as, for example, splines 308 engageable with an arm 310, as described herein. Rack 302 includes an arm 312 extending from end 304. In some embodiments, arm 312 is attached with rack 302 with, for example, with clips, hooks, adhesives and/or flanges.

Arm 312 includes a surface that defines an opening 314 configured for disposal of protrusion 120 for connecting compressor/distractor 300 to implant support. Arm 310 is axially translatable along axis Al relative to arm 312. Arm 310 includes a surface that defines an opening 318 configured for disposal of protrusion 120 for connecting compressor/distractor 300 to implant support 14a.

Compressor/distractor 300 includes a ratchet, which includes splines 308 and arm 310 engageable in a bi-directional and/or two-way ratchet configuration. Arm 310 includes a latch 320, which is engageable selectively with splines 308. In various embodiments the latch 320 includes a pinion or pawl (not shown in detail) engageable with splines 308.

Latch 320 is pivotable relative to arm 310 for disposal selectively in one or multiple positions. In various embodiments the positions include a distraction position, a neutral position, and a compression position. In the distraction position, latch 320 engages rack 302 to allow axial and/or incremental translation of arm 310 relative to arm 312/rack 302, in the direction shown by arrows B in FIG. 19. As such, distraction of vertebral tissue connected with implant supports 14, 14a can be performed. Latch 320 is pivotable relative to arm 310 for disposal in a neutral position (not shown). In the neutral position, latch 320 disengages from rack 302 to allow free axial translation of arm 310 relative to arm 312/rack 302.

Figure 9:
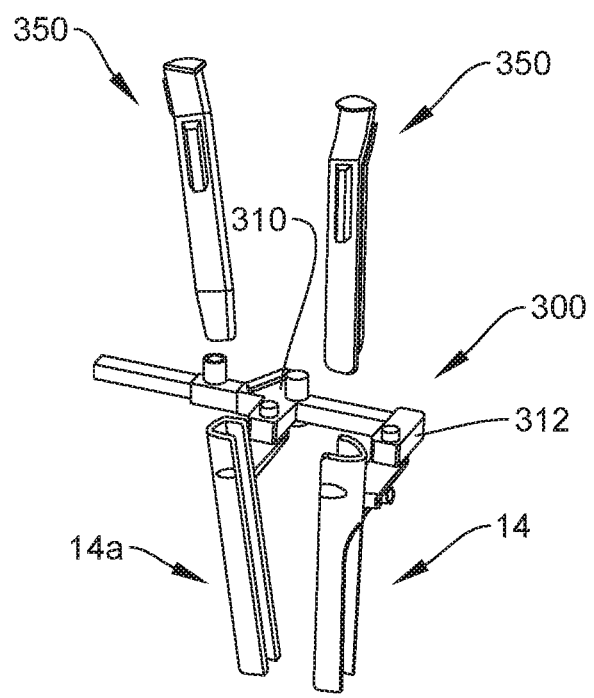
FIG. 9 is a perspective view of components of one embodiment of a surgical system in accordance with the principles of the present disclosure with some of the parts separated.
Figure 10:
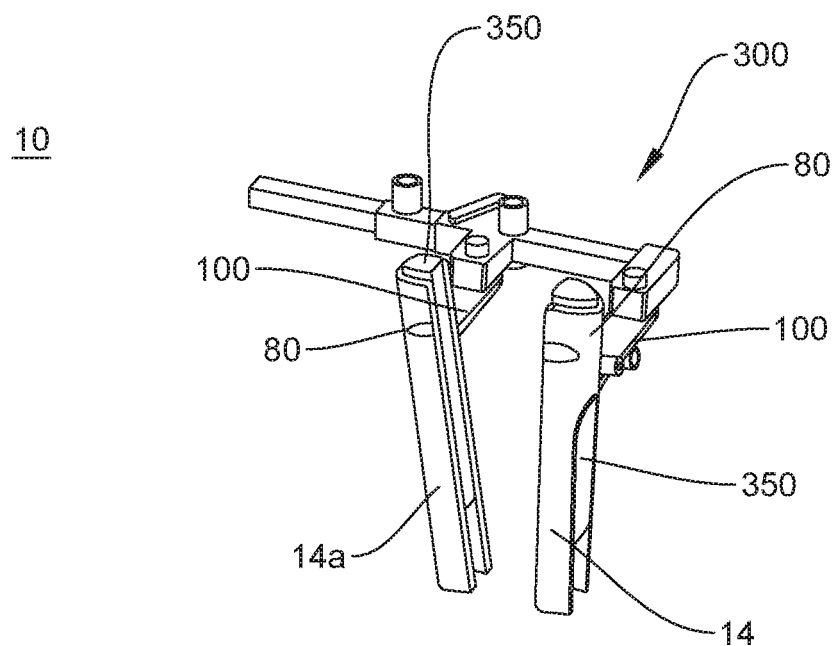
FIG. 10 is a perspective view of components of one embodiment of a surgical system in accordance with the principles of the present disclosure.

In some embodiments, surgical system 10 includes one or more alignment guides 350, as shown in FIGS. 9 and 10. Each guide 350 is configured for disposal with receiver 18 of one or more bone fasteners 16 to orient implant supports 14, 14a with respect to receiver 18 and to facilitate identifying, locating and/or engaging implant supports 14, 14a with receiver 18.

Figure 26:
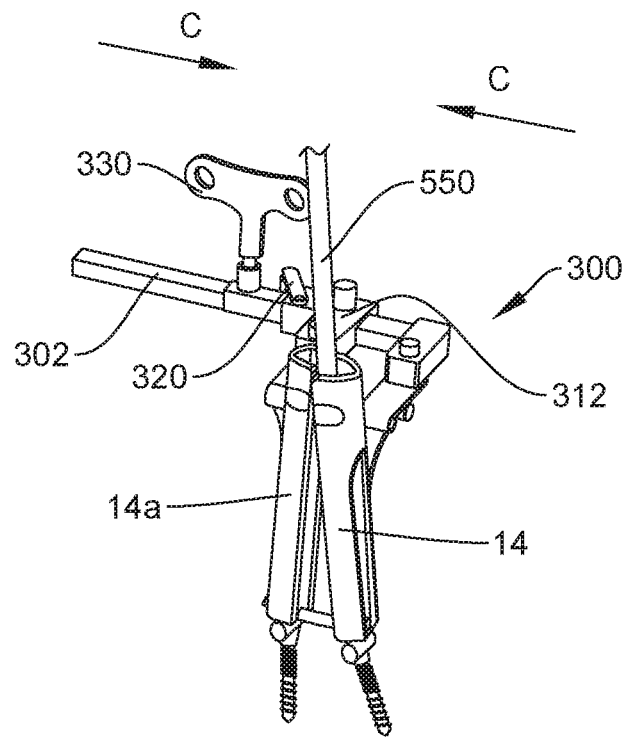
FIG. 26 is a perspective view of components of one embodiment of a surgical system disposed with vertebrae in accordance with the principles of the present disclosure.
Figure 27:
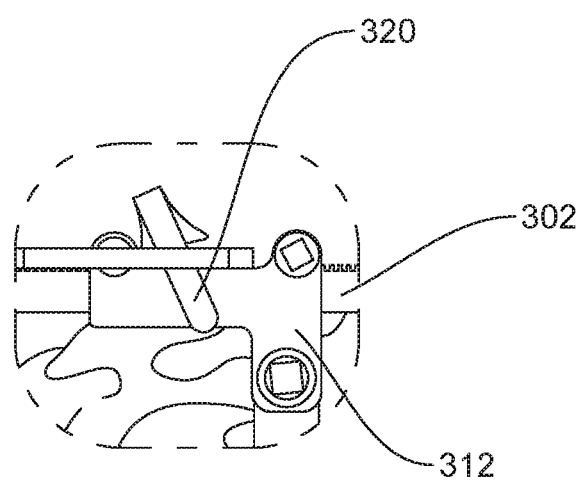
FIG. 27 is a plan view of components shown in FIG. 26.

Latch 320 is pivotable relative to arm 310 for disposal in a compression position, as shown in FIG. 26. In the compression position, latch 320 engages rack 302 to allow axial and/or incremental translation of arm 310 relative to arm 312/rack 302, in the direction shown by arrows C. As such, compression of vertebral tissue connected with implant supports 14, 14a can be performed. In some embodiments, a rotatable key 330 includes a gear surface engageable with splines 308 to axially and/or incrementally translate rack 302 to facilitate distraction and/or compression, as described herein.

In some embodiments, connection of implant supports 14, 14a to facilitate correction of a vertebral angle of vertebrae, for example, to achieve a selected lordosis and/or kyphosis, via manipulation of implant supports 14, 14a, as described herein. In some embodiments, implant supports 14, 14a are connected with compressor/distractor 300 to maintain a corrected vertebral angle of vertebrae during distraction and/or compression, as described herein.

In assembly, operation and use, surgical system 10, similar to the systems and methods described herein, is employed with a surgical procedure, for treatment of a spine of a patient including vertebrae V, as shown in FIGS. 11-30. Surgical system 10 may also be employed with surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

Figure 12:
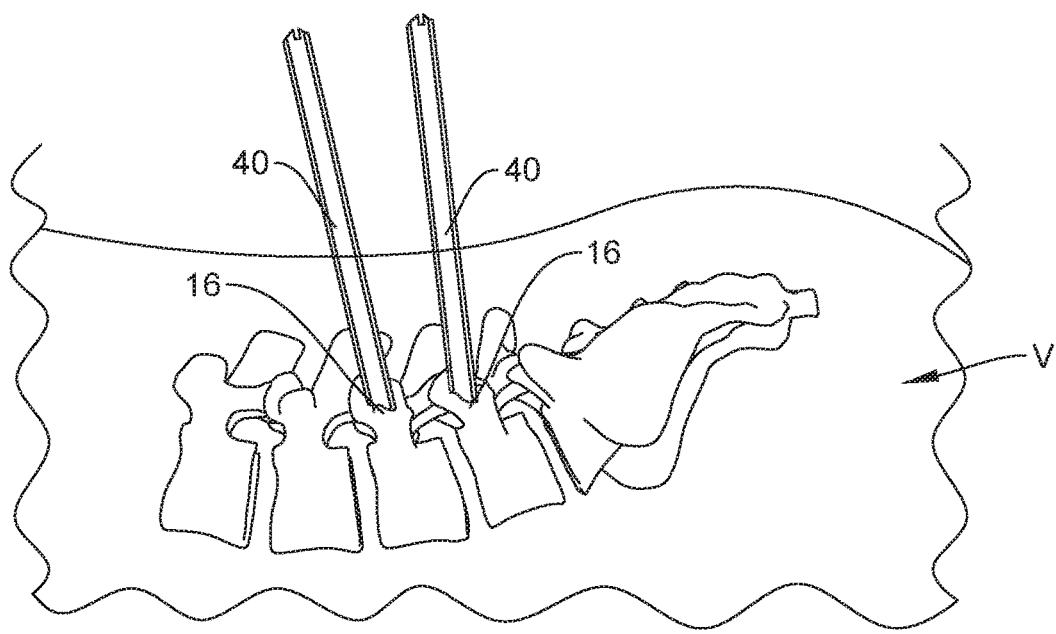
FIG. 12 is a side view of components of one embodiment of a surgical system in accordance with the principles of the present disclosure disposed with vertebrae.

Surgical system 10 is employed with a procedure for treatment of an applicable condition or injury of an affected section of a spinal column and adjacent areas within a body. For example, vertebrae V includes a vertebral level V1, a vertebral level V2 and a vertebral level V3, as shown in FIG. 12. Diseased and/or damaged vertebrae and intervertebral discs are disposed at vertebra V2 between vertebrae V1 and V3. In some embodiments, components of surgical system 10 are configured for insertion with a vertebral space to space apart articular joint surfaces, provide support and maximize stabilization of vertebrae V.

Figure 11:
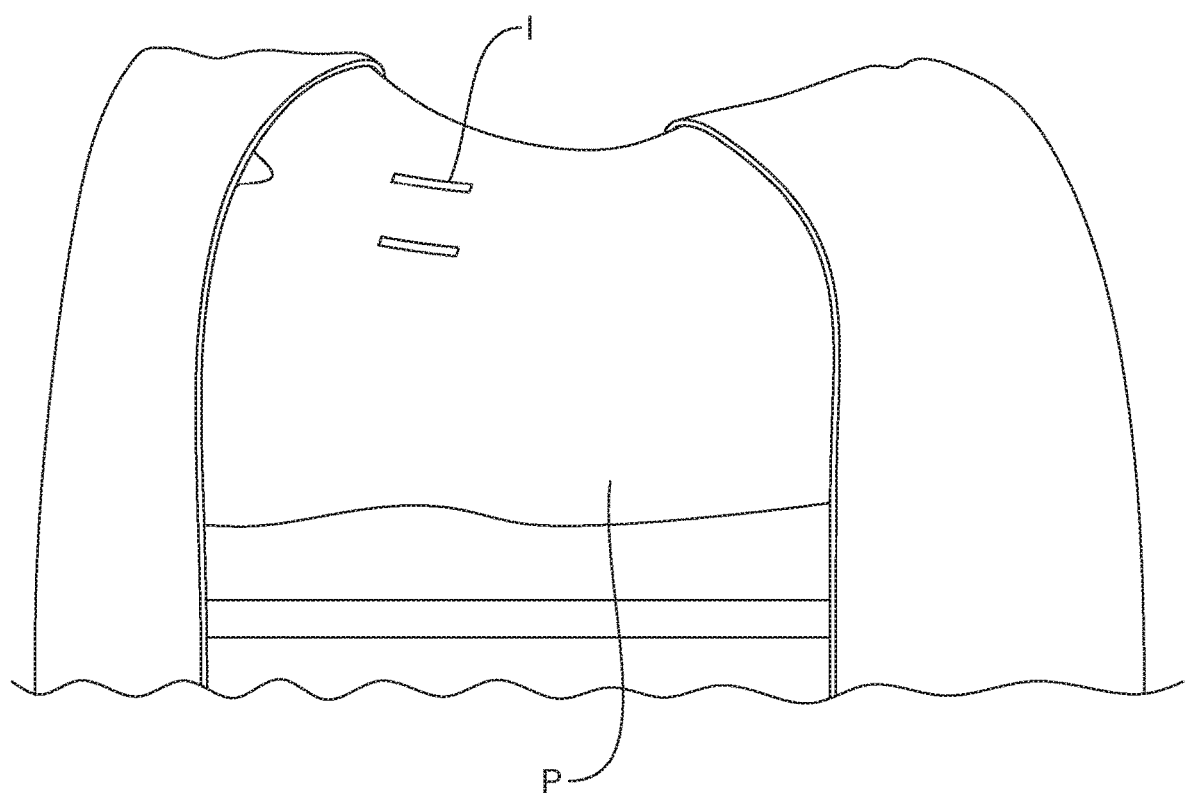
FIG. 11 is a perspective view of a patient body.

In use, to treat the affected section of vertebrae V, a medical practitioner obtains access to a surgical site including vertebrae V in any appropriate manner, such as through incision and retraction of tissues, as shown in FIG. 11. In some embodiments, surgical system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area.

Figure 13:
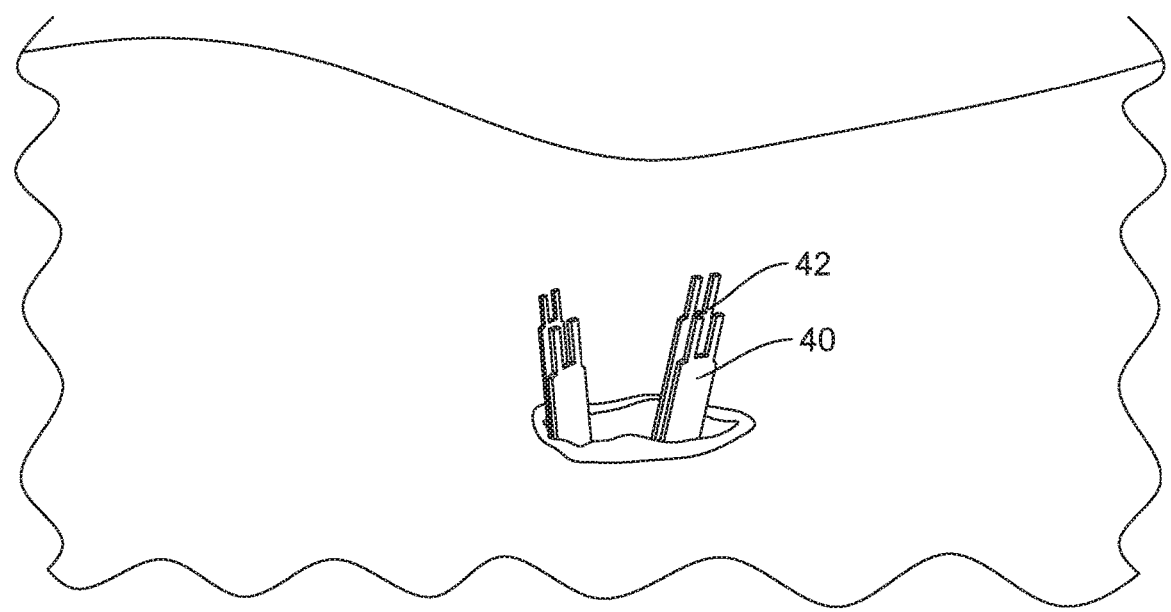
FIG. 13 is a perspective view of components of one embodiment of a surgical system in accordance with the principles of the present disclosure.
Figure 14:
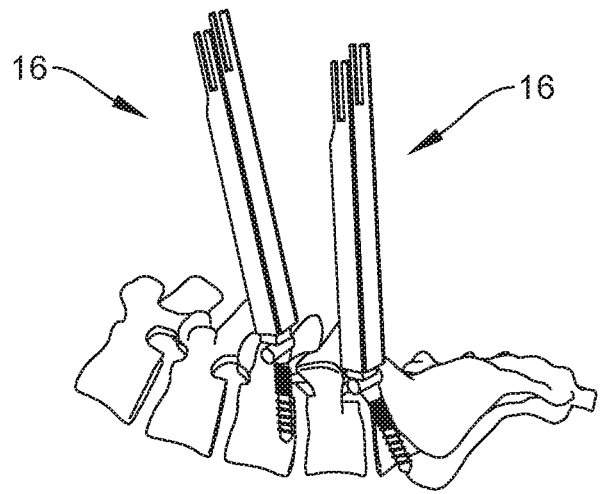
FIG. 14 is a perspective view of components of one embodiment of a surgical system disposed with vertebrae in accordance with the principles of the present disclosure.

An incision I is made in the body of a patient P and a cutting instrument (not shown) creates a surgical pathway for implantation of components of surgical system 10, as shown in FIGS. 12-14. A preparation instrument (not shown) can be employed to prepare tissue surfaces of vertebrae V, as well as for aspiration and irrigation of a surgical region.

Pilot holes or the like are made in selected vertebrae V1 and V3 for receiving bone fasteners 16. A driver (not shown) is disposed adjacent vertebrae V at a surgical site and is manipulated to drive, torque, insert or otherwise connect bone fasteners 16 with vertebrae V1 and V3. Bone fasteners 16 are engaged with vertebrae V along a lateral side L of vertebrae V, as shown in FIG. 12. Extenders 40, 42 are engaged with bone fasteners 16.

Figure 15:
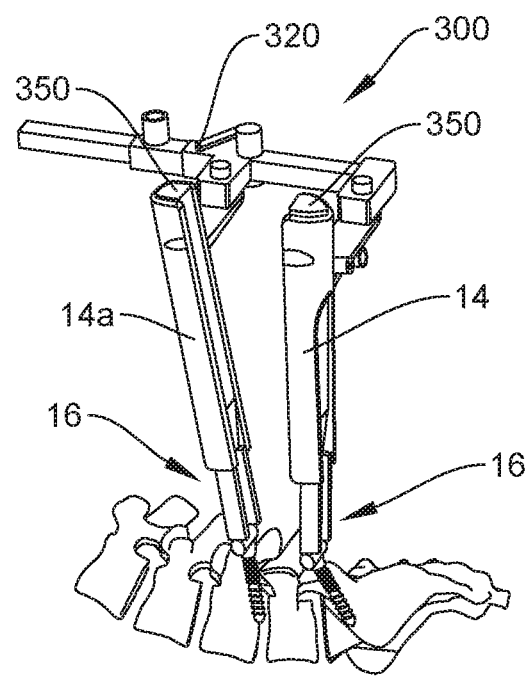
FIG. 15 is a perspective view of components of one embodiment of a surgical system disposed with vertebrae disposed with a patient body in accordance with the principles of the present disclosure.

Implant supports 14, 14a are connected with extenders 40, 42, as described herein. Compressor/distractor 300 is mounted with adaptors 100 via protrusion 120 for fixation therewith, as described herein. Connectors 80 capture extenders 40, 42, as shown in FIG. 15 and described herein. Compressor/distractor 300 is connected with implant supports 14, 14a to allow for distraction and/or compression of vertebrae V connected with extenders 40, 42.

Figure 16:
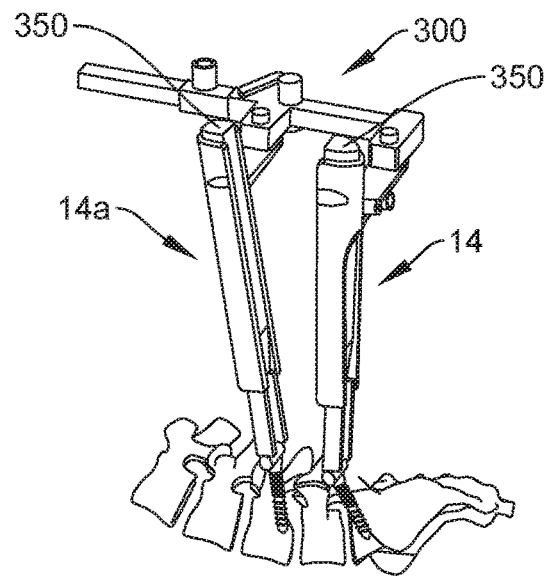
FIG. 16 is a perspective view of components of one embodiment of a surgical system disposed with vertebrae in accordance with the principles of the present disclosure.
Figure 17:
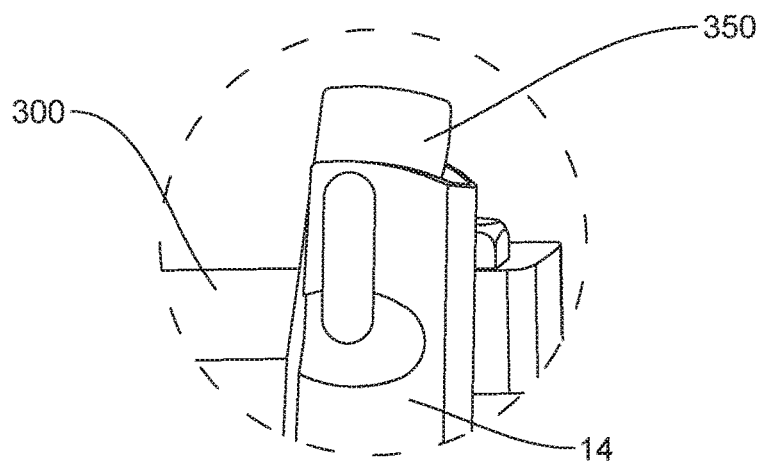
FIG. 17 is an enlarged view of detail A shown in FIG. 16.

Guide 350 is disposed with (e.g., within) connector 80. Guide 350 is translated into engagement with bone fastener 16 until fully seated with receiver 18. Guide 350 is configured to orient implant supports 14, 14a and facilitate identifying, locating and/or engaging implant supports 14, 14a with receiver 18, as shown in FIGS. 15-17.

Figure 18:
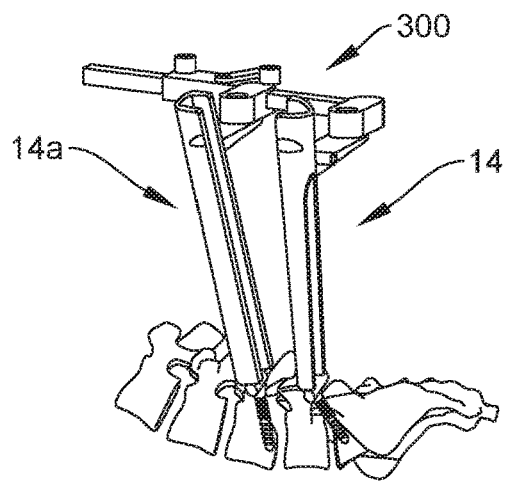
FIG. 18 is a perspective view of components of one embodiment of a surgical system disposed with vertebrae in accordance with the principles of the present disclosure.
Figure 19:
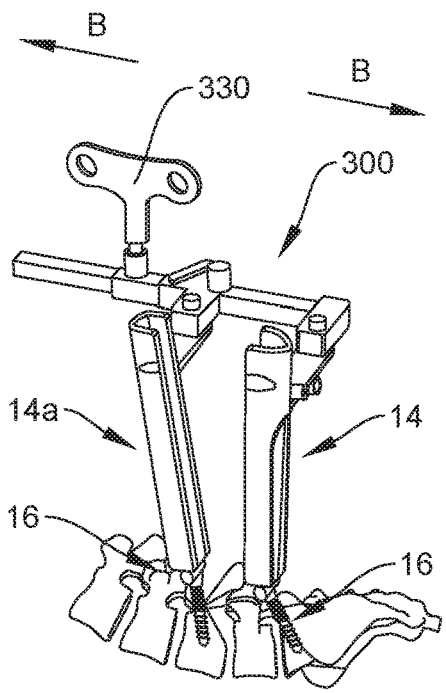
FIG. 19 is a perspective view of components of one embodiment of a surgical system disposed with vertebrae in accordance with the principles of the present disclosure.
Figure 20:
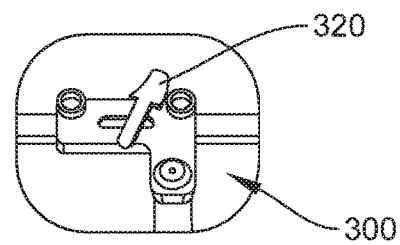
FIG. 20 is an enlarged view of detail B shown in FIG. 19.

Latch 320 is pivotable relative to arm 310 for disposal in a distraction position, as shown in FIGS. 18-20. In the distraction position, latch 320 engages rack 302 to allow axial and/or incremental translation of arm 310 relative to arm 312/rack 302, in the direction shown by arrows B in FIG. 16, to distract vertebral tissue connected with implant supports 14, 14a. The applied distraction forces on bone fasteners 16 will allow for opening of the foramen and the posterior wall of the spinal disc. Latch 320 can be released or re-adjusted at any time during the procedure. Latch 320 is pivotable relative to arm 310 for disposal in a neutral position (not shown). In the neutral position, latch 320 allows free axial translation of arm 310 relative to arm 312/rack 302.

Figure 21:
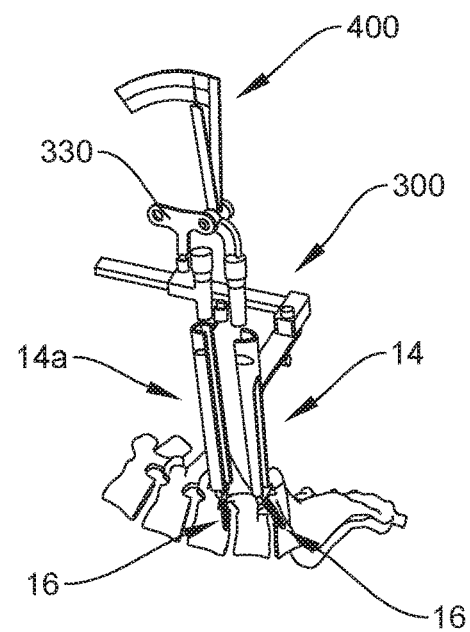
FIG. 21 is a perspective view of components of one embodiment of a surgical system disposed with vertebrae in accordance with the principles of the present disclosure.
Figure 22:
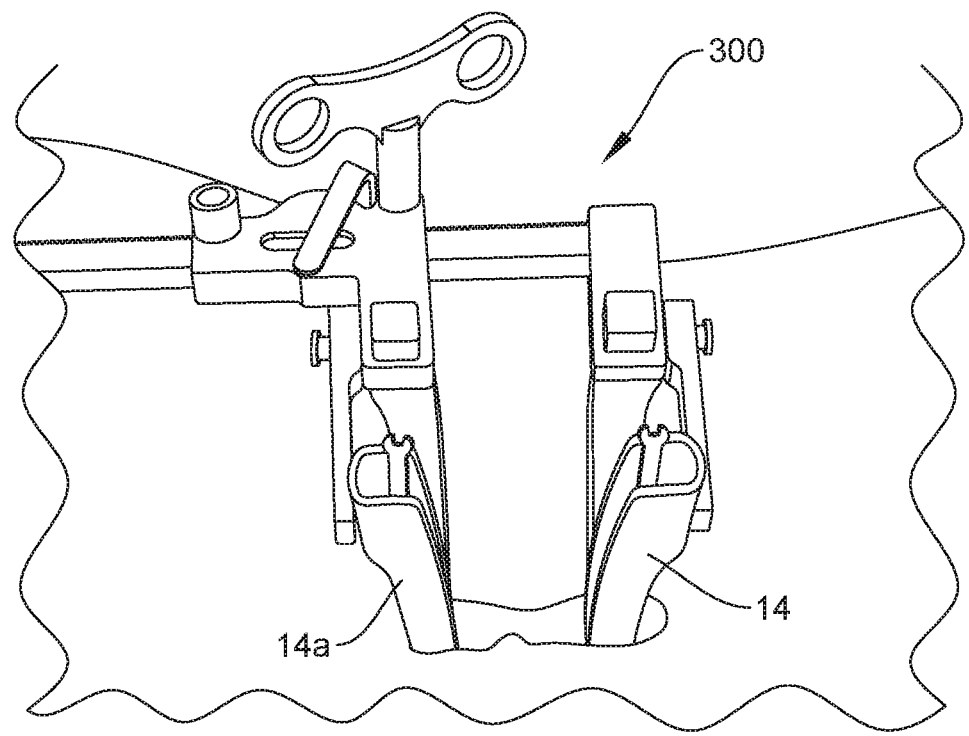
FIG. 22 is a plan view of components of one embodiment of a surgical system disposed with a patient body in accordance with the principles of the present disclosure.
Figure 23:
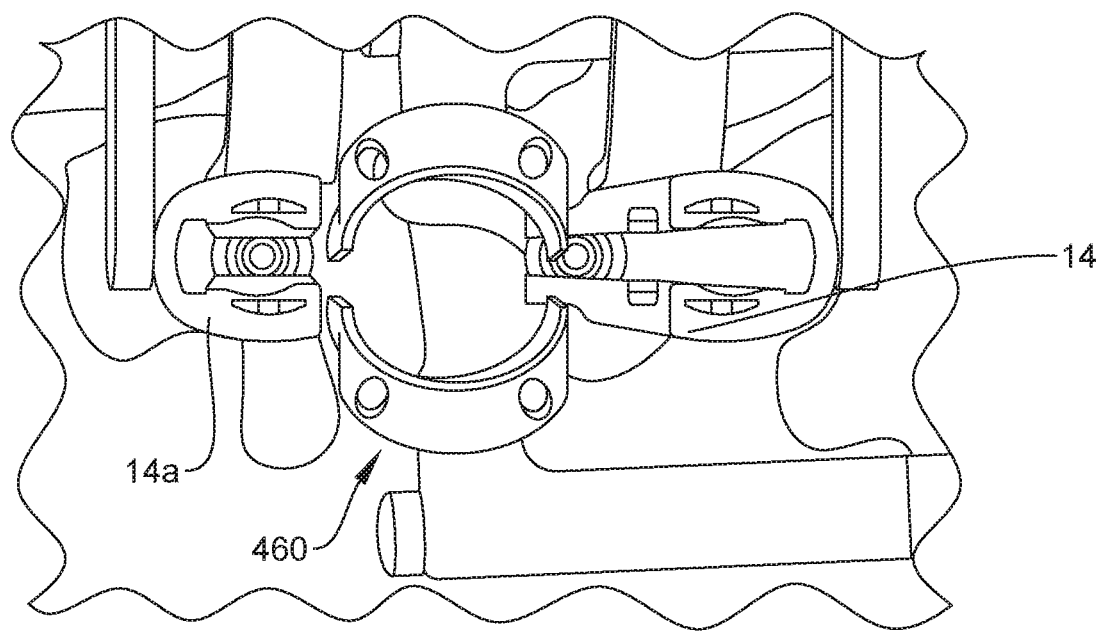
FIG. 23 is a plan view of components of one embodiment of a surgical system disposed with vertebrae in accordance with the principles of the present disclosure disposed with vertebrae.

In some embodiments, a measuring device, such as, for example, a caliper 400 is utilized to determine a length of spinal rod 450, as shown in FIG. 21. Caliper 400 is engaged with implant supports 14, 14a such that a distance between bone fasteners 16 can be determined. Determining the distance provides a length of rod 450 for connection with bone fasteners 16. In some embodiments, a retractor 460, as shown in FIG. 23, is disposed with tissue to form a surgical passageway to facilitate insertion of a spinal implant, such as, for example, an interbody spinal implant.

In some embodiments, a rod inserter 500 is engaged with spinal rod 450, as shown in FIG. 24. Rod inserter 500 directs and/or guides spinal rod 450 through slots 70 and into receiver 18. In some embodiments, a percutaneous endoscopic lumbar discectomy is utilized.

Figure 25:
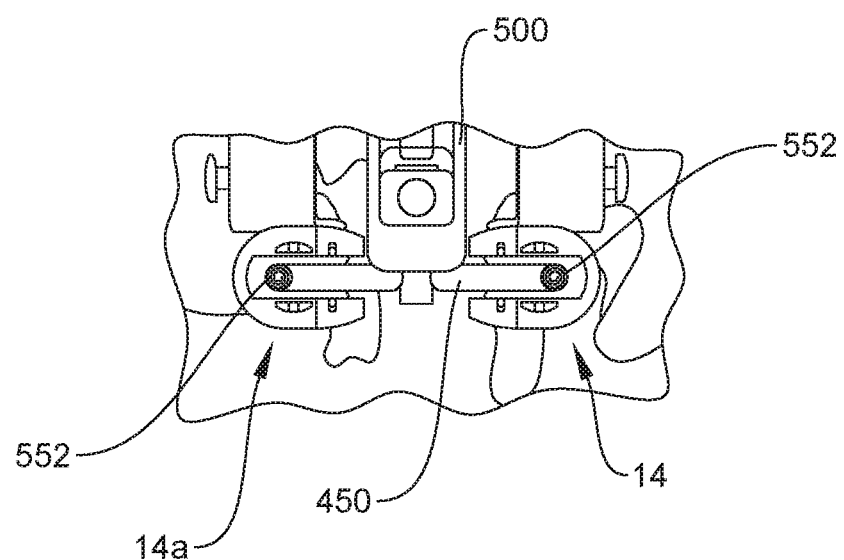
FIG. 25 a plan view of components shown in FIG. 24.

In some embodiments, a driver 550 is utilized to engage a set screw 552 with bone fasteners 16, as shown in FIGS. 24 and 25. Driver 550 directs and/or guides set screw 552 through each of implant supports 14, 14a into engagement with receivers 18. Set screw 552 engages receivers 18 to fix spinal rod 450. In some embodiments, if segmental compression is required, set screws 552 are loosened and latch 320 is pivotable relative to arm 310 for disposal in a compression position, as shown in FIGS. 26-28A. In the compression position, latch 320 engages rack 302 to allow axial and/or incremental translation of arm 310 relative to arm 312/rack 302, in the direction shown by arrows C, to compress vertebral tissue connected with implant supports 14, 14a. In some embodiments, a rotatable key 330 includes a gear surface engageable with splines 308 to axially and/or incrementally translate rack 302 to facilitate distraction and/or compression, as described herein. In some embodiments, adaptor 100 is pivotally connected to connector 80 such that connectors 80 can be rotated and/or angled, as shown in FIGS. 26-28A, to facilitate compression.

Figure 28:
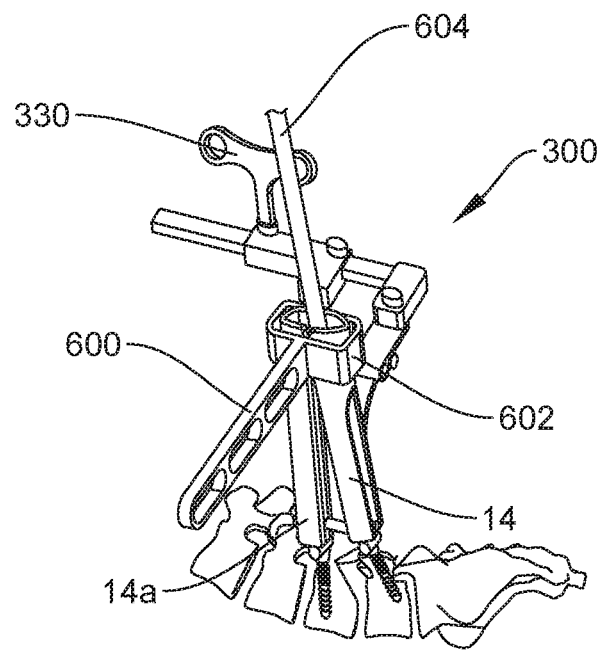
FIG. 28 is a perspective view of components of one embodiment of a surgical system disposed with vertebrae in accordance with the principles of the present disclosure.
Figure 28A:
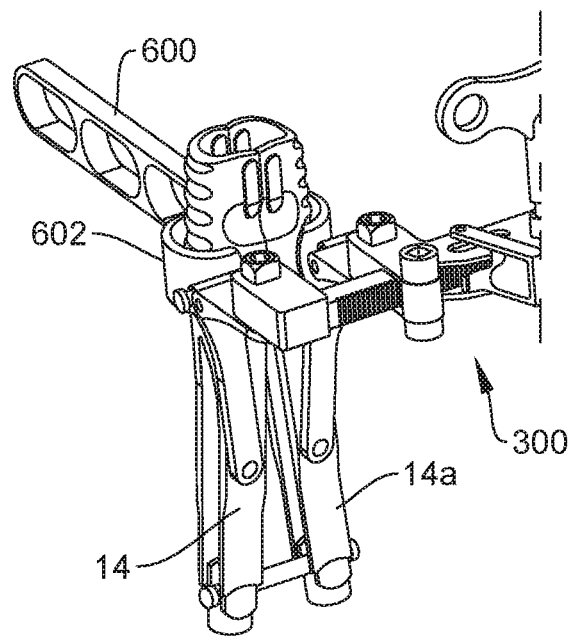
FIG. 28A is a perspective view of components of one embodiment of a surgical system in accordance with the principles of the present disclosure.
Figure 29:
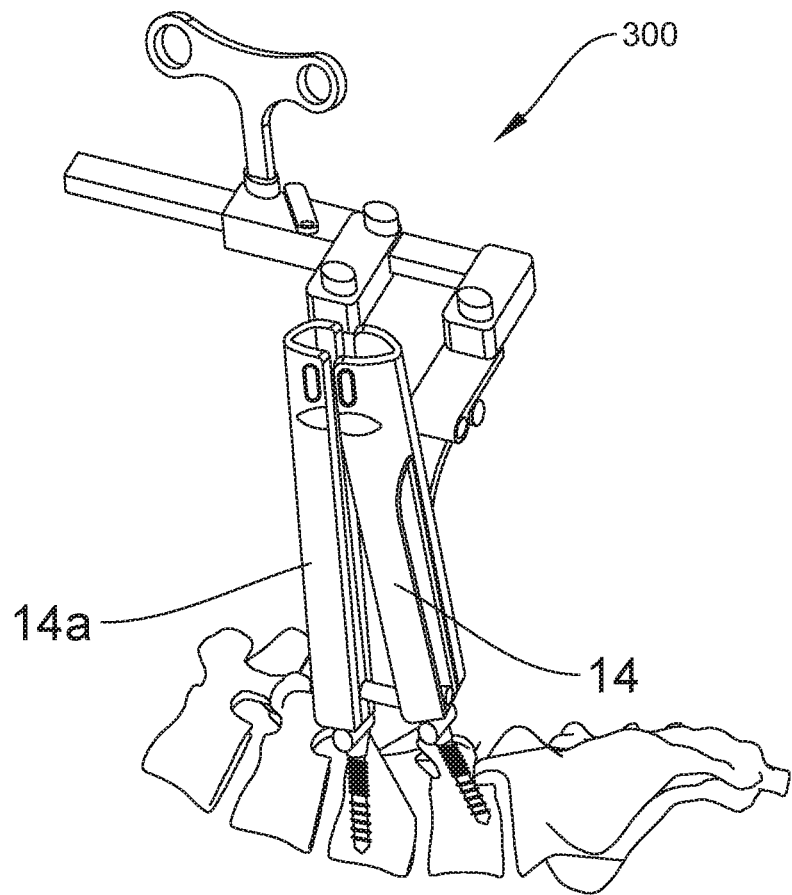
FIG. 29 is a perspective view of components of one embodiment of a surgical system disposed with vertebrae in accordance with the principles of the present disclosure.
Figure 30:
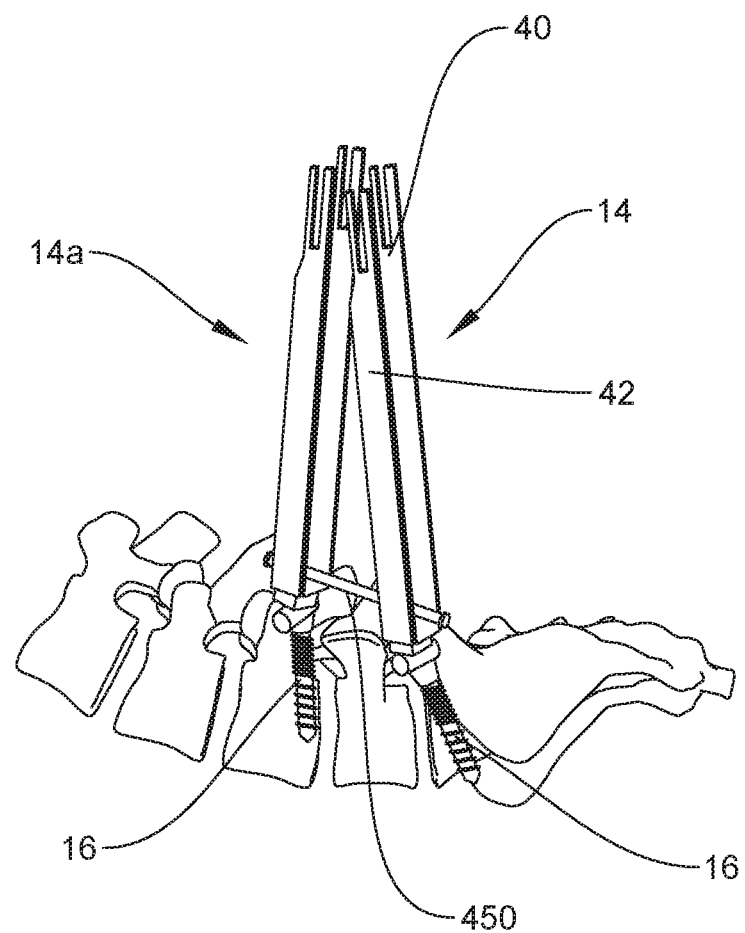
FIG. 30 is a perspective view of components of one embodiment of a surgical system disposed with vertebrae in accordance with the principles of the present disclosure.

In some embodiments, a tab hook counter torque handle 600 and a tab hook counter torque sleeve 602 are engaged with implant supports 14, 14a, as shown in FIGS. 28 and 28A. Handle 600 and sleeve 602 are configured to provide additional leverage to facilitate removing and/or separating a frangible or break off portion of set screw 552 at a selected torque limit. In some embodiments, counter torque sleeve 602 is configured to reinforce connection of connectors 80 and protect break-away tabs 34, 36 during break off of set screw 552. In some embodiments, connectors 80 are disposed in contact at a center of a radius of a pre-bent rod. In some embodiments, a break off handle 604 is disposed with driver 500 and is manipulated to apply a force to set screw 552 for tightening and the torque limit for break off. Compressor/distractor 300 and implant supports 14, 14a are removed, as shown in FIGS. 29 and 30. Vertebrae V is aligned to a selected orientation for sagittal, coronal and/or axial correction.

Upon completion of a procedure, as described herein, the surgical instruments, assemblies and non-implanted components of surgical system 10 are removed and the incision(s) are closed. One or more of the components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10. In some embodiments, surgical system 10 may include one or a plurality of plates, connectors and/or bone fasteners for use with a single vertebral level or a plurality of vertebral levels.

Figure 31:
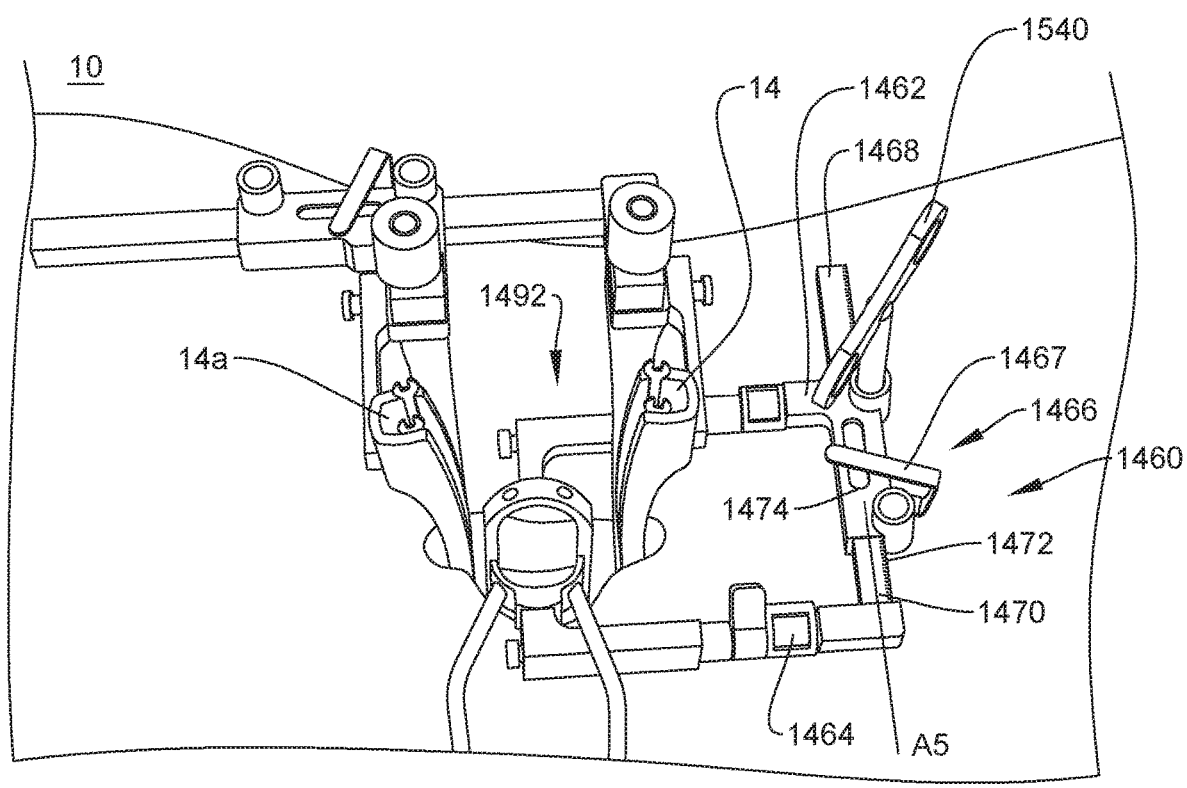
FIG. 31 is a top perspective view of components of one embodiment of a surgical system disposed with a patient body in accordance with the principles of the present disclosure.

In one embodiment, surgical system 10, similar to the components and methods described herein, includes a retractor 1460, as shown in FIGS. 31-36, compressor/distractor 300 and implant supports 14, 14a. Retractor 1460 can in any way to be like retractor 460 described herein. Retractor 1460 includes a first member, such as, for example, a first arm 1462 and a second member, such as, for example, a second arm 1464. Arms 1462, 1464 are connected by a longitudinal element, such as, for example, a ratchet 1466, as shown in FIG. 31.

Ratchet 1466 extends between an end 1468 and an end 1470, defining a longitudinal axis A5. Ratchet 1466 is configured to connect arms 1462, 1464 to each other and translate arm 1464 relative to arm 1462. Ratchet 1466 includes an outer surface having a plurality of teeth, such as, for example, splines 1472, engageable with a portion 1474 of ratchet 1466, as described herein. Ratchet 1466 includes a latch 1467 that is movable, for example, pivotable, relative to portion 1474 to dispose and/or fix arm 1464 relative to arm 1462 in one or multiple positions.

Figure 33:
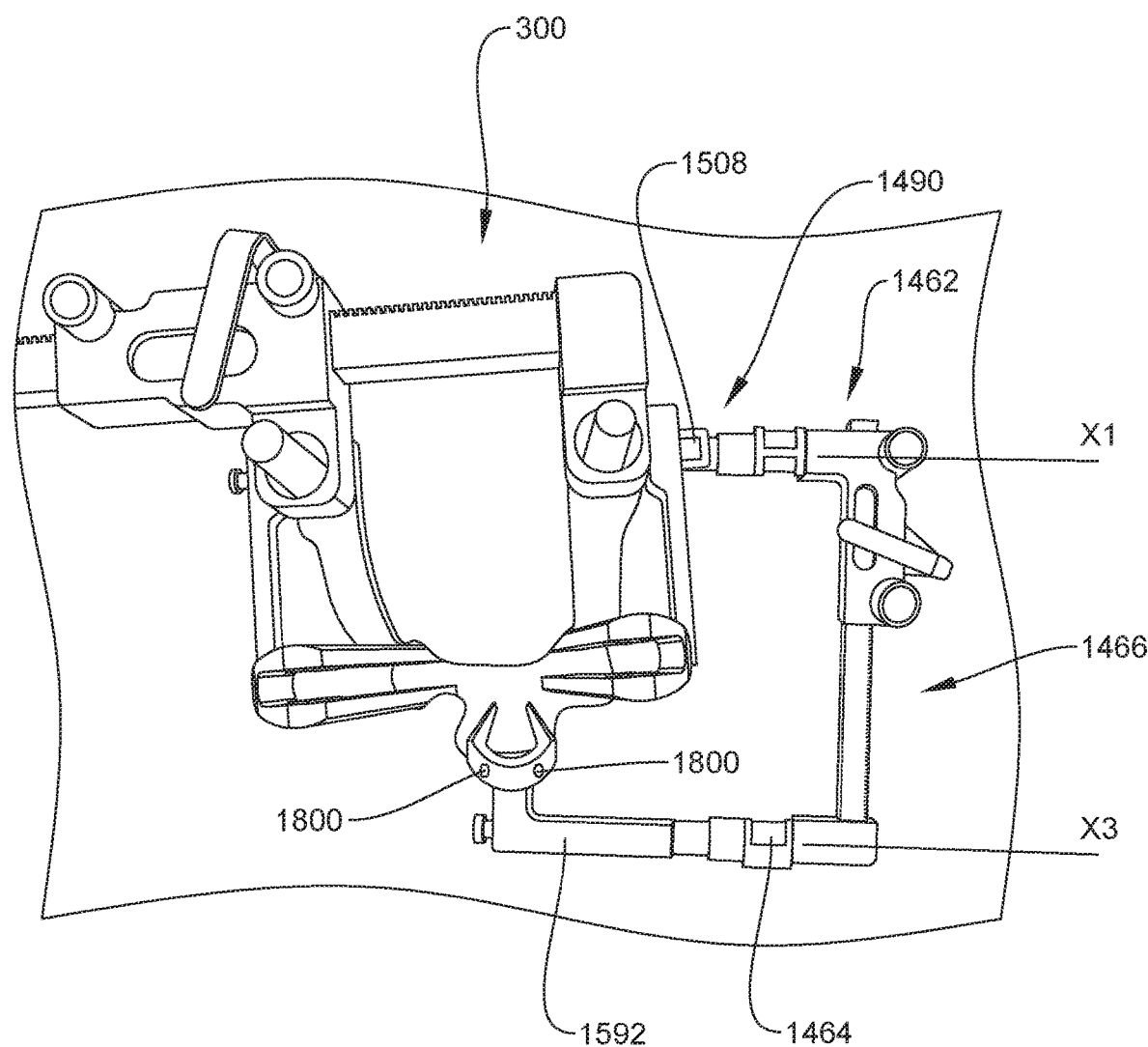
FIG. 33 is a plan view of components of one embodiment of a surgical system disposed with a patient body in accordance with the principles of the present disclosure.

In various embodiments, one of arms 1462, 1464 is fixedly connected to the ratchet 1466. In the embodiment of FIG. 31, arm 1464 is. The fixed arm can extend from anywhere at or between ends 1468, 1470. In FIG. 31, the arm 1464 extends from end 1470 of ratchet 1466. Arm 1464 defines an axis X3, as shown in FIG. 33. Arm 1464 includes a mating surface, such as, for example, an opening (not shown) configured for connection with a blade 1592, as described herein.

The opening or arm 1464 to facilitate rotation of blade 1592 about axis X3, as described herein. Blade 1592 includes an inner surface and an outer surface configured for engagement with tissue. In some embodiments, all or only a portion of blade 1592 may have various cross-section configurations, such as, for example, arcuate, cylindrical, oblong, rectangular, polygonal, undulating, irregular, uniform, non-uniform, consistent, variable, and/or U-shape. Blade 1592 is movable within multiple dimensions to space tissue selectively. Latch 1467 is movable or otherwise pivotable, as mentioned, to dispose and/or fix arm 1464 relative to arm 1462 in one or multiple positions, causing blade 1592 to be fixed in a selected orientation with respect to at least one degree of freedom.

Figure 34:
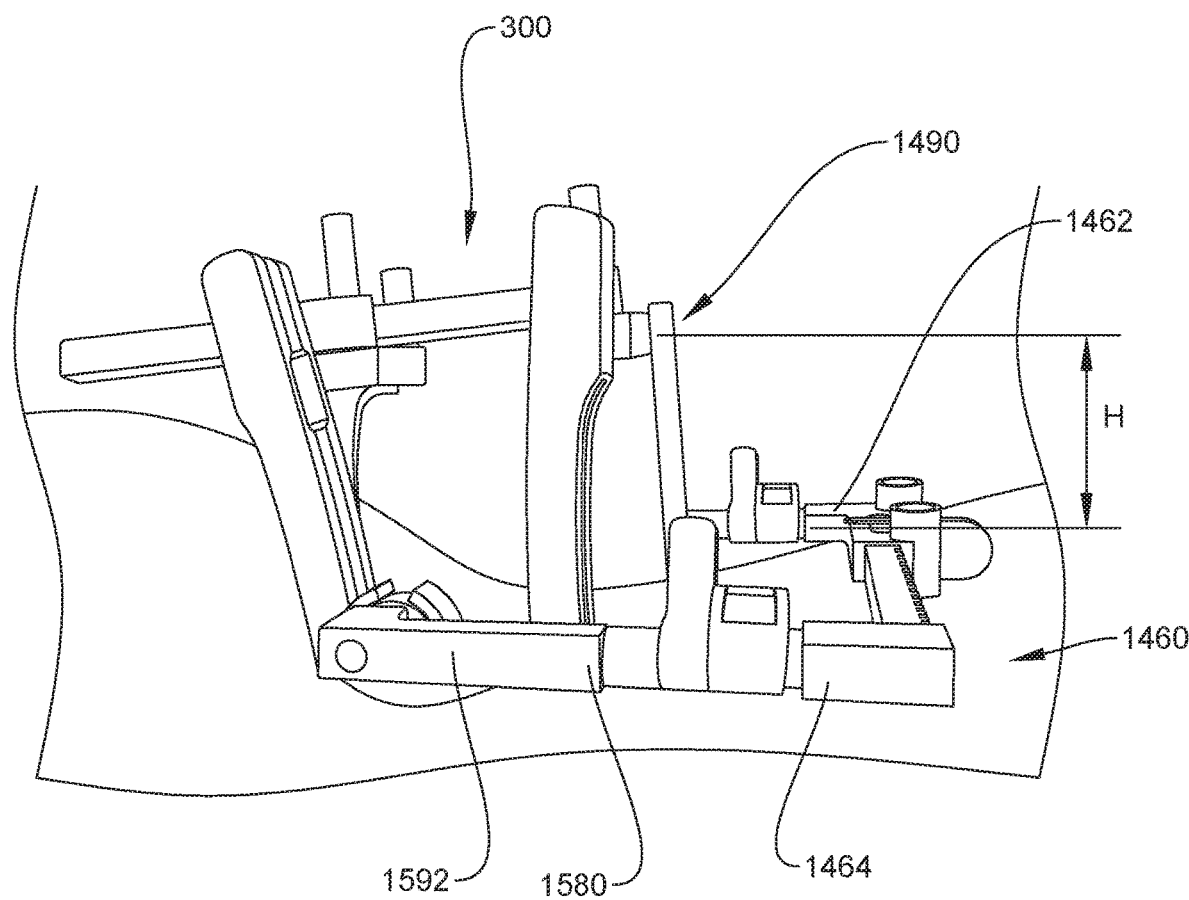
FIG. 34 is a side view of components of one embodiment of a surgical system disposed with a patient body in accordance with the principles of the present disclosure.
Figure 35:
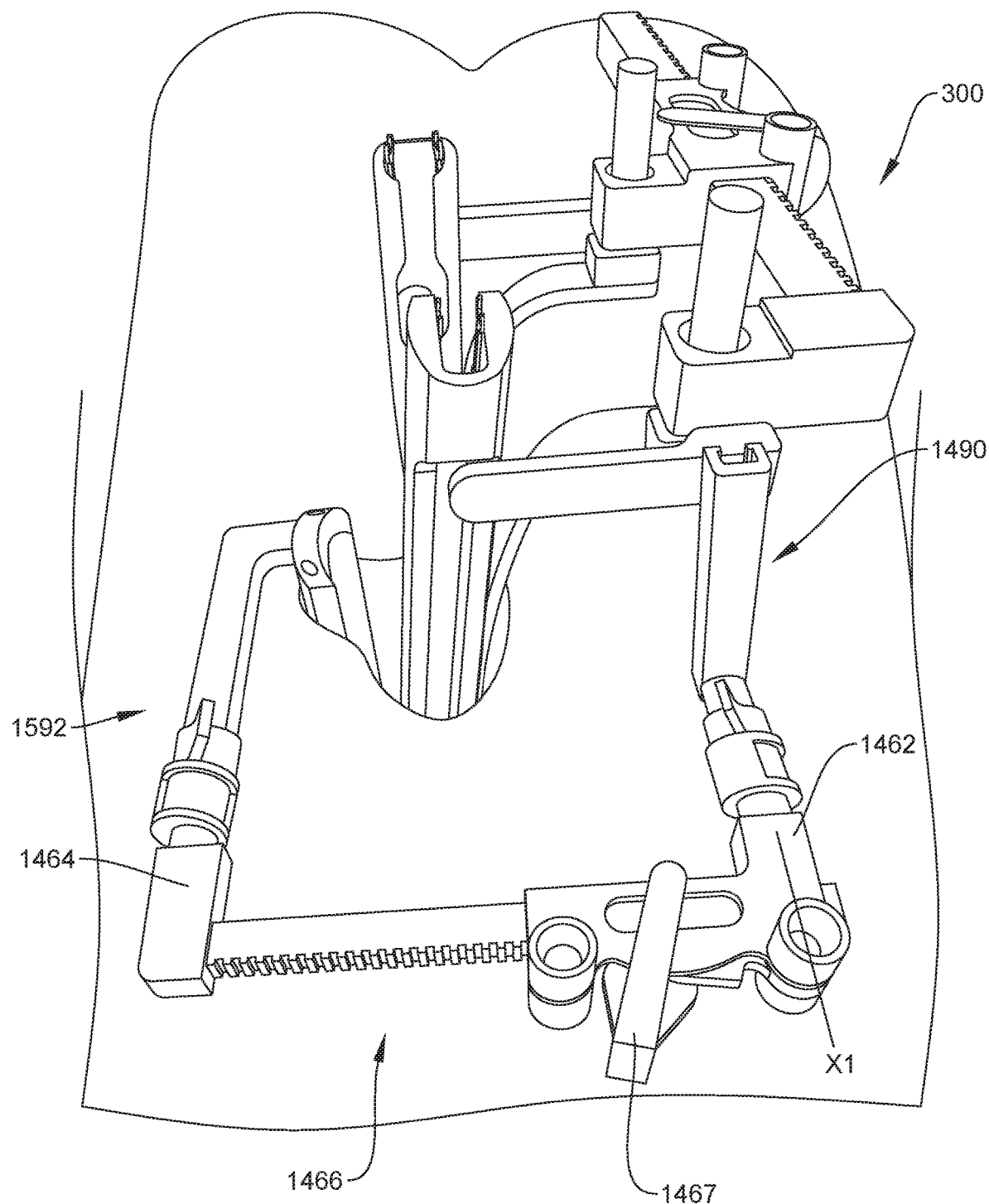
FIG. 35 is a perspective view of components of one embodiment of a surgical system disposed with a patient body in accordance with the principles of the present disclosure.
Figure 36:
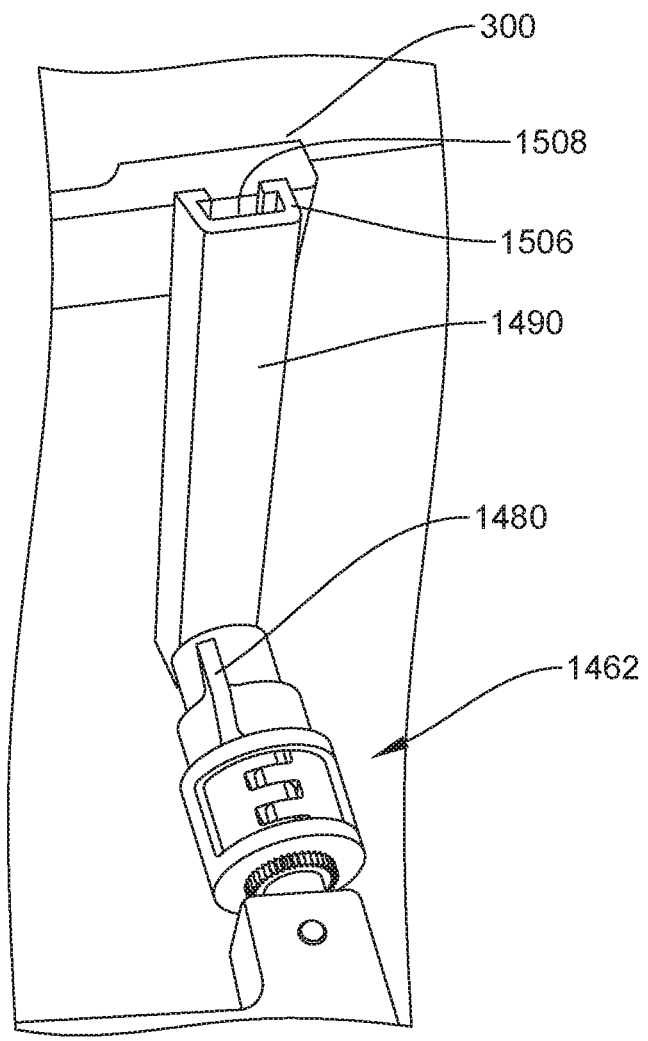
FIG. 36 is a perspective view of components of one embodiment of a surgical system disposed with a patient body in accordance with the principles of the present disclosure.
Figure 37:
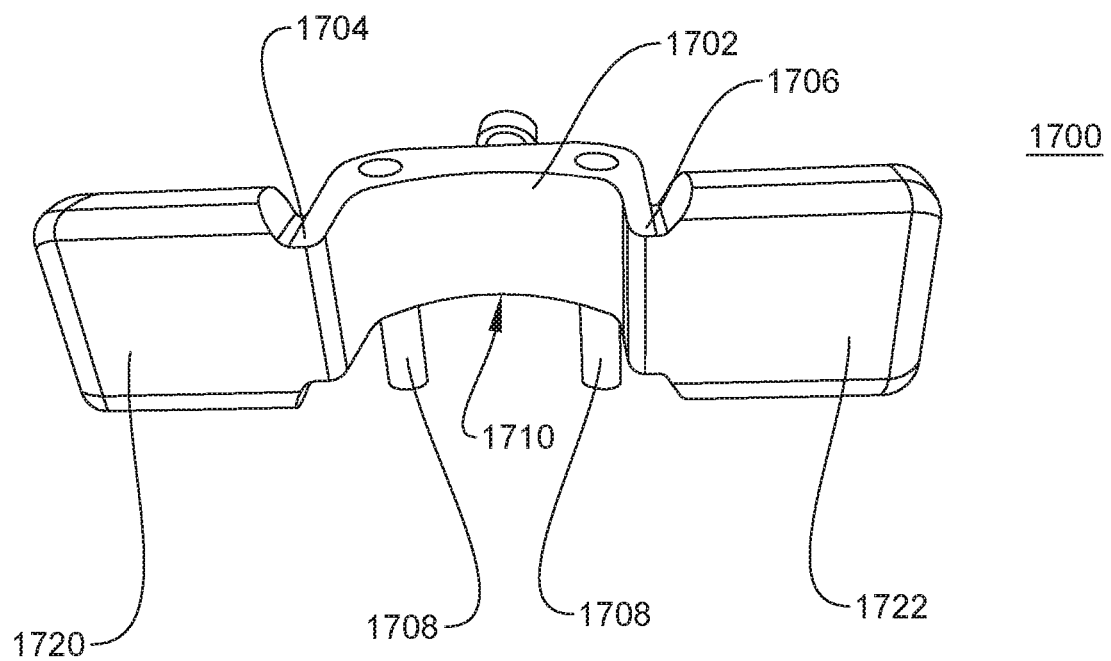
FIG. 37 is a perspective view of components of one embodiment of a surgical system disposed with vertebrae in accordance with the principles of the present disclosure.
Figure 38:
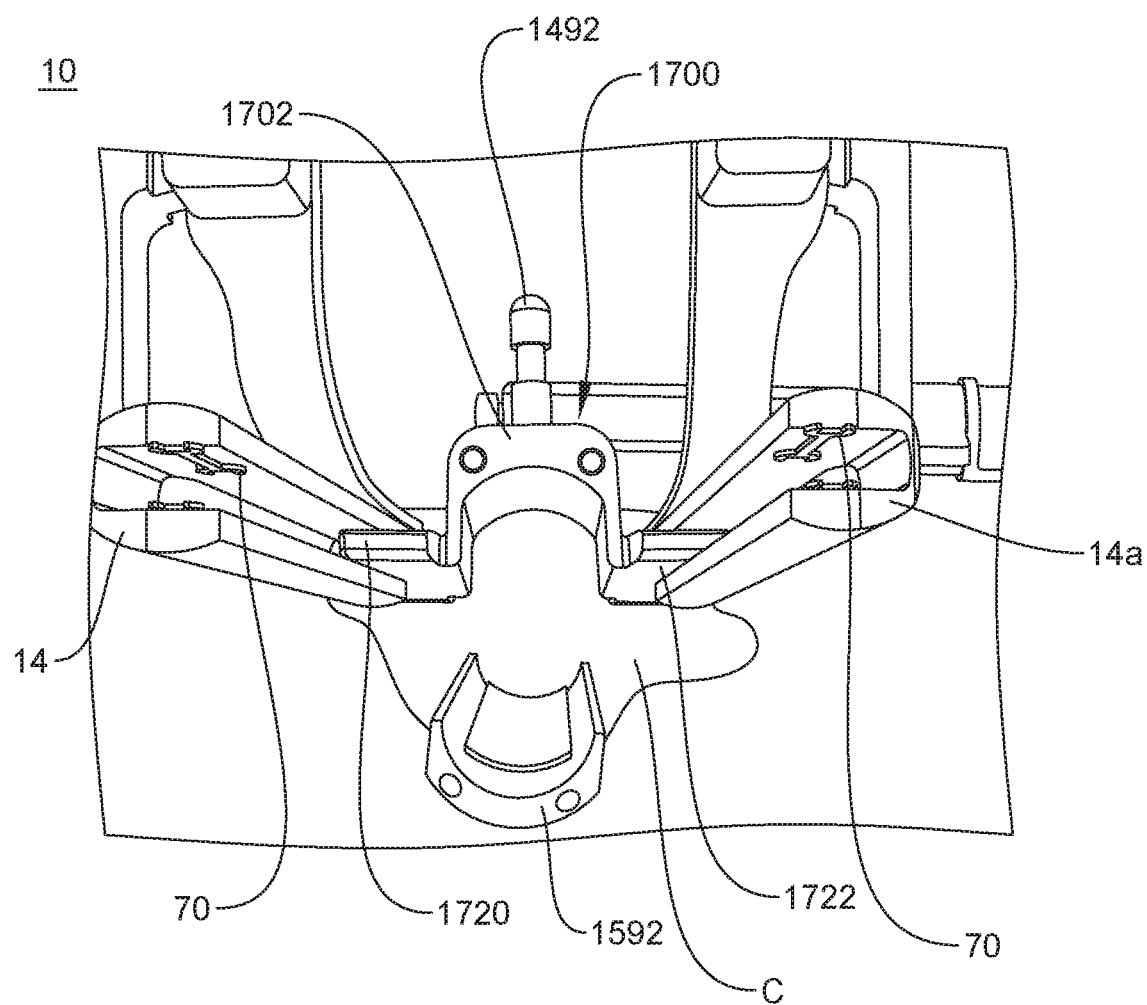
FIG. 38 is a plan view of components of one embodiment of a surgical system disposed with a patient body in accordance with the principles of the present disclosure.
Figure 39:
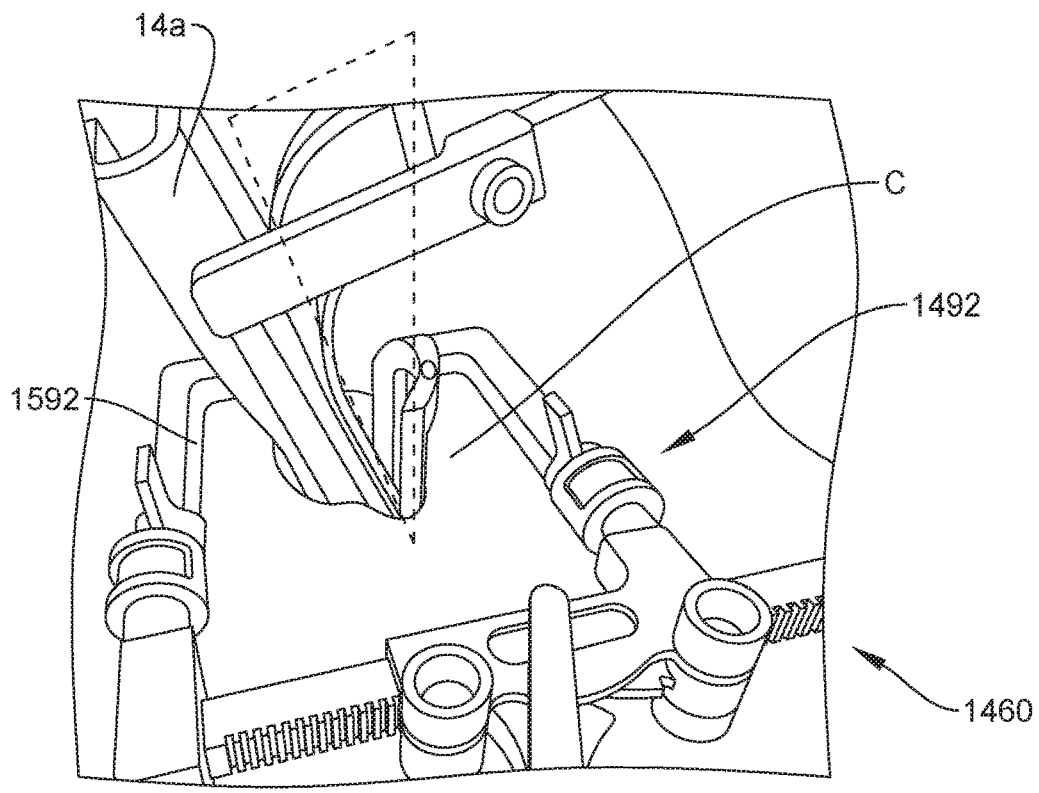
FIG. 39 is a perspective view of components of one embodiment of a surgical system disposed with a patient body in accordance with the principles of the present disclosure.
Figure 40:
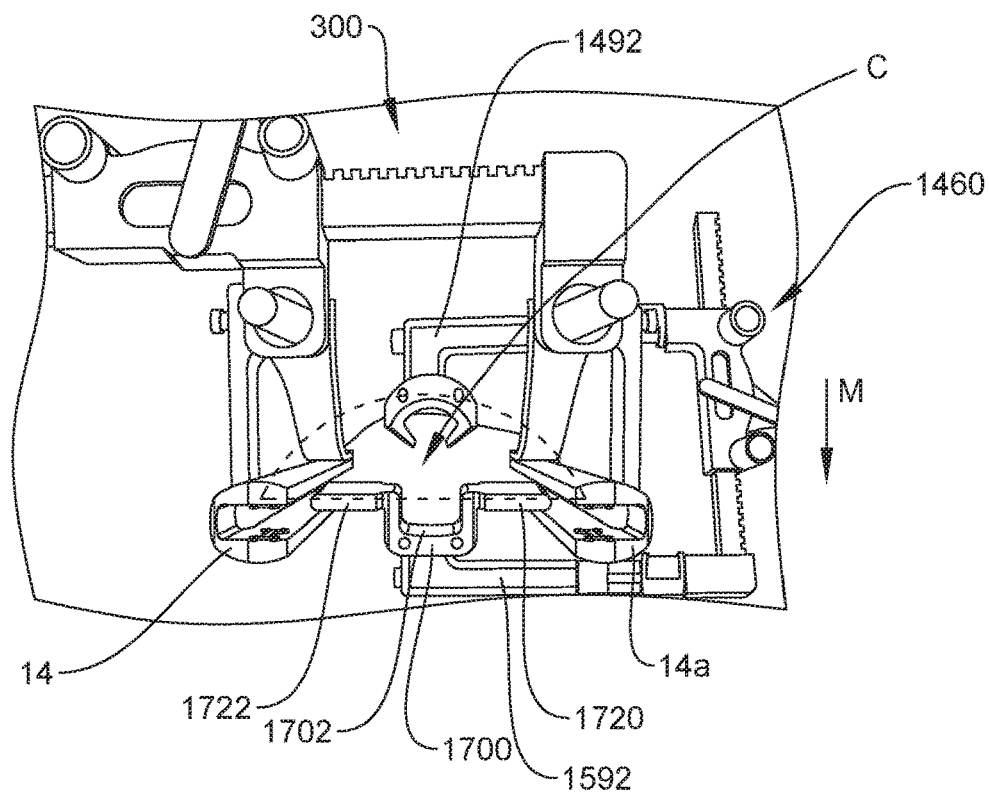
FIG. 40 is a plan view of components of one embodiment of a surgical system disposed with a patient body in accordance with the principles of the present disclosure.

Arm 1462 extends from end 1468, or between end 1468 and end 1470, of ratchet 1466. Arm 1462 defines an axis X1, as shown in FIG. 33. Arm 1462 includes a mating surface, such as, for example, an opening 1480, as shown in FIG. 36. Opening 1480 is configured to be connectable with a part, such as a height controller 1490, and/or a blade 1492, as described herein. Height controller 1490 is configured to adjust a height H of retractor 1460 and/or blade 1592 relative to compressor/distractor 300, as shown in FIGS. 34 and 35.

As an aside, the manner by which dimensions or directions are indicated does not limit scope of the invention, such as limiting the orientation that any component may be disposed, connected, or moved. Here, for instance, reference to the height controller and height do not limit that component and dimension to a strictly vertical orientation in surgery.

Figure 32:
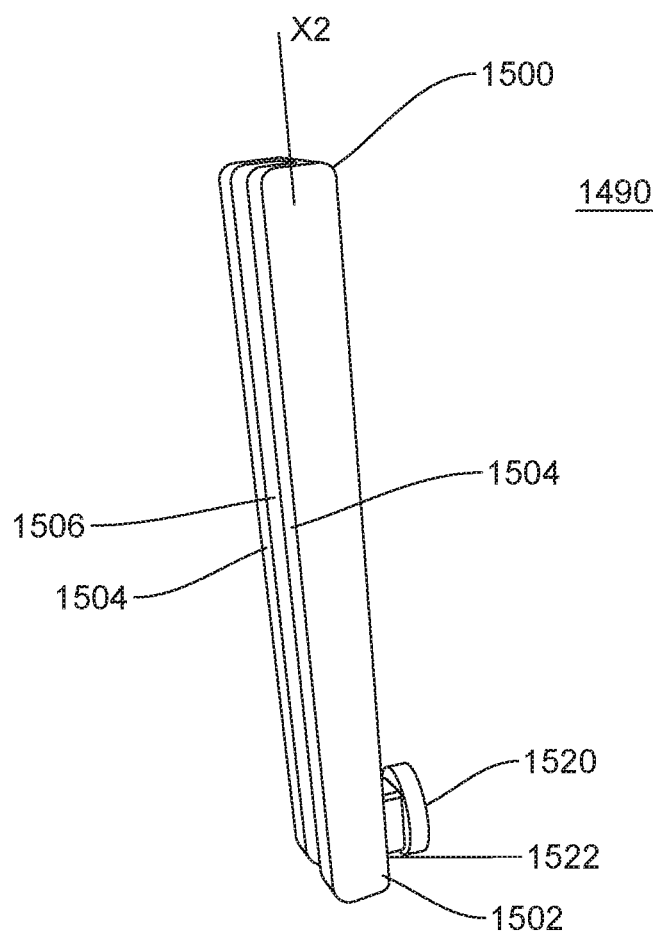
FIG. 32 is a perspective view of components of one embodiment of a surgical system in accordance with the principles of the present disclosure.

Height controller 1490 extends between a first end 1500 and a second end 1502 defining an axis X2, as shown in FIG. 32. In various embodiments, height controller 1490 includes longitudinal rails 1504 that define a longitudinal groove 1506. Groove 1506 extends along axis X2 between ends 1500, 1502. In some embodiments, groove 1506 may be disposed at alternate orientations, relative to axis X2, such as, for example, transverse, perpendicular and/or other angular orientations such as acute or obtuse, coaxial and/or may be offset or staggered. In some embodiments, height controller 1490 includes one or a plurality of rails 1504.

Groove 1506 is configured for disposal of an element, such as, for example, a projection 1508 extending from compressor/distractor 300, as shown in FIGS. 33 and 36. Projection 1508 is slidably translatable within groove 1506 to facilitate translation of height controller 1490 along compressor/distractor 300. Height controller 1490 is selectively fixable in a position relative to compressor/distractor 300. In some embodiments, height controller 1490 is selectively fixable relative to compressor/distractor 300 via a friction fit engagement between a surface of groove 1506 and a configuration, such as a tapered configuration, of projection 1508, such as, for example, a dove tail configuration. In a contemplated embodiment, the interface—i.e., the groove 1506 and the projection 1508—is configured to provide haptic feedback, such as a clicking feeling, as the protrusion is translated within the groove.

As mentioned, translation of height controller 1490 along compressor/distractor 300 facilitates adjustment of height H of retractor 1460 and/or blade 1592 relative to compressor/distractor 300. In some embodiments, height H is adjustable in a range of about 0 mm to about 50 mm relative to compressor/distractor 300.

In various embodiments, end 1502 includes a protrusion 1520 extending from a surface 1522 of height controller 1490, as shown in FIG. 32. Protrusion 1520 extends perpendicular to axis X2. In some embodiments, protrusion 1520 may extend at alternate orientations relative to axis X2, such as, for example, transverse and/or other angular orientations such as acute or obtuse, coaxial and/or may be offset or staggered. Protrusion 1520 matingly engages opening 1480 of arm 1462. In various embodiments, protrusion 1520 is releasably engageable with opening 1480. In some embodiments, protrusion 1520 is engageable with opening 1480 in a snap-fit connection. Engagement of protrusion 1520 with opening 1480 orients height controller 1490 transverse to axis X1, as shown in FIG. 35. In some embodiments, height controller 1490 may extend at alternate orientations relative to axis X1, such as, for example, perpendicular and/or other angular orientations such as acute or obtuse, coaxial and/or may be offset or staggered.

Blade 1492 includes a pivot surface (not shown) engageable with opening 1480 to facilitate rotation of blade 1492 about axis X1, as described herein. Blade 1492 and height controller 1490 are interchangeable with arm 1462. Blade 1492 includes an inner surface and an outer surface configured for engagement with tissue. In some embodiments, all or only a portion of blade 1492 may have various cross-section configurations, such as, for example, arcuate, cylindrical, oblong, rectangular, polygonal, undulating, irregular, uniform, non-uniform, consistent, variable, and/or U-shape. In some embodiments, as shown in FIG. 31, retractor 1460 includes a handle 1540 disposed with arm 1462 to facilitate rotation of blade 1492 about axis X1.

In one embodiment, surgical system 10 includes a stability element 1700, as shown in FIGS. 37-42. Stability element 1700 is configured for disposal with slots 70 (FIGS. 4 and 5) of implant supports, 14, 14*a*, as described herein. Stability element 1700 is configured to stabilize lateral movement of one or more components of surgical system 10, for example, implant supports 14, 14*a*, blade 1492 or blade 1592, and/or components of retractor 1460, relative to a patient body.

Stability element 1700 includes a body 1702 that extends between a first end 1704 and a second end 1706. Body 1702 includes a configuration for a mating engagement with the inner surface of blade 1492 and/or blade 1592. In some embodiments, all or only a portion of body 1702 may have various cross-section configurations, such as, for example, arcuate, cylindrical, oblong, rectangular, polygonal, undulating, irregular, uniform, non-uniform, consistent, variable, and/or U-shape.

In various embodiments, body 1702 includes a surface 1710. Mating pins 1708 extend from surface 1710. Pins 1708 are configured for engagement with openings 1800 (FIG. 33) disposed with blade 1492 and/or blade 1592. In some embodiments, body 1702 includes at least one mating pin 1708.

End 1704 is connected to a flange 1720 extending therefrom. Flange 1720 is configured for disposal with slot 70 of implant support 14 and/or implant support 14*a*. End 1706 is connected to a flange 1722 extending therefrom. Flange 1722 is configured for disposal with slot 70 of implant support 14 and/or implant support 14*a*. Flanges 1720, 1722 are configured for slidable translation within slots 70 to facilitate positioning of stability element 1700.

For example, in some embodiments, retractor 1460 is provided to maintain tissue in a medial-lateral orientation creating a channel C (FIGS. 41 and 42) for accessing the spine anatomy. In some embodiments, retractor 1460 is provided to maintain tissue in a plurality of blade angles on both a lateral and dorsal axis. Stability element 1700 is utilized to space apart tissue and/or open channel C in a medial and/or lateral direction. For example, stability element 1700 is positioned such that body 1702 is disposed in a mating configuration with blade 1592, as described herein. Flange 1722 is disposed with slot 70 of implant support 14. Flange 1720 is disposed with slot 70 of implant support 14*a*. In this orientation, stability element 1700 moves blade 1592 and implant supports 14, 14*a* medially, such as for example, toward a midline of the patient's body, as shown by arrow M in FIG. 40. Movement of blade 1592 and implant supports 14, 14*a* in the medial direction opens channel C toward the midline of the patient body.

Figure 41:
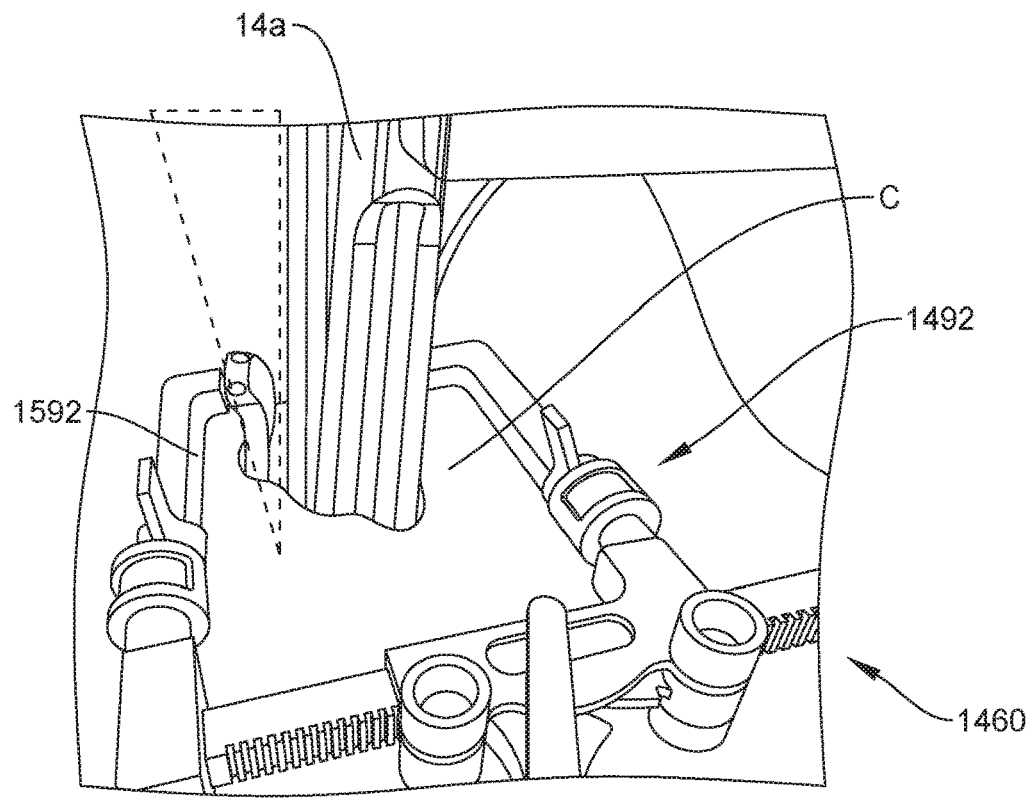
FIG. 41 is a perspective view of components of one embodiment of a surgical system disposed with a patient body in accordance with the principles of the present disclosure.
Figure 42:
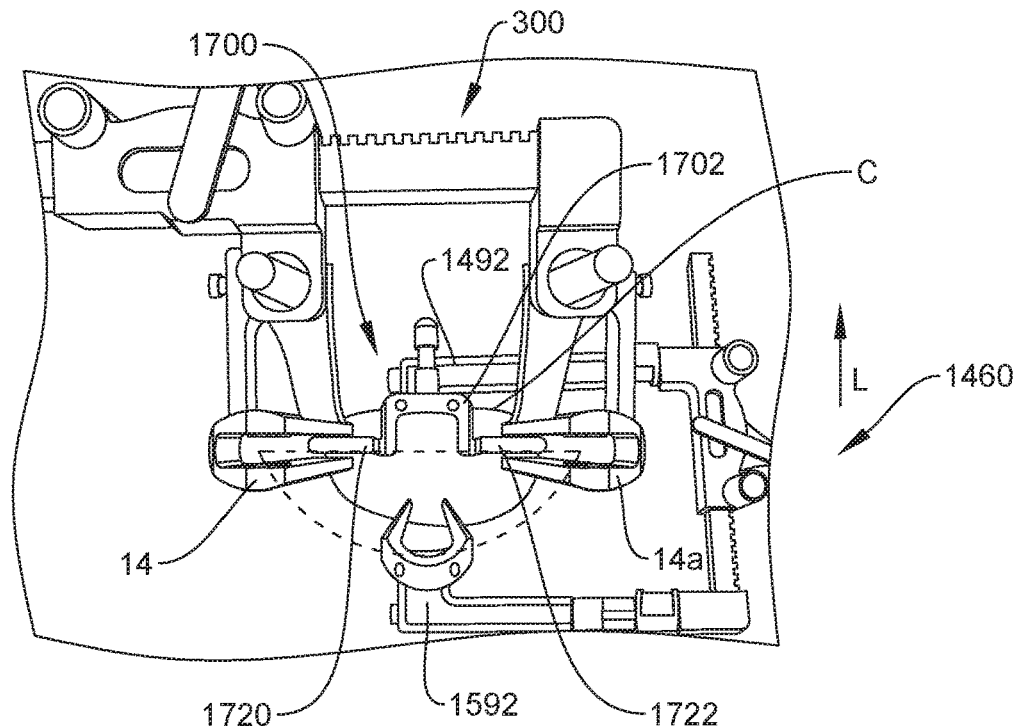
FIG. 42 is a plan view of components of one embodiment of a surgical system disposed with a patient body in accordance with the principles of the present disclosure.

In some embodiments, stability element 1700 is utilized to space apart tissue and/or open channel C in the lateral direction. For example, stability element 1700 is positioned such that body 1702 is disposed in a mating configuration with blade 1492, as shown in FIGS. 41 and 42. Flange 1720 is disposed with slot 70 of implant support 14. Flange 1722 is disposed with slot 70 of implant support 14*a*. In this orientation, stability element 1700 moves blade 1492 and implant supports 14, 14*a* laterally, such as for example, away from the midline and toward a lateral side of the patient's body, as shown by arrow L in FIG. 42. Movement of blade 1492 and implant supports 14, 14*a* in the lateral direction opens channel C toward the lateral side of the patient body.

In some embodiments, surgical system 10 includes one or a plurality of alternative surgical instruments, each configured for mating engagement in a quick release configuration with spinal constructs, as described herein. This configuration facilitates the interchangeability of the spinal constructs with the alternative surgical instruments. In some embodiments, surgical system 10 includes one or a plurality of alternative surgical instruments, such as, for example, inserters, extenders, reducers, spreaders, distractors, blades, retractors, clamps, forceps, elevators and drills, which may be alternatively sized and dimensioned, and arranged as a kit.

In some embodiments, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the components and/or surfaces of surgical system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a retractor comprising: a first member comprising a first arm and a second member comprising a second arm;
   a surgical distractor; and
   a height controller, the height controller being connectable with the distractor and the first member,
   wherein the surgical distractor comprises a projection and the height controller includes a longitudinal rail defining a groove, the projection being disposed in the groove such that the height controller is configured to translate the first member relative to the surgical distractor to adjust a height of the retractor relative to the surgical distractor.

2. A surgical instrument as recited in claim 1, wherein the height controller is slidably translatable along the surgical distractor.

3. A surgical instrument as recited in claim 1, wherein the height controller is selectively fixable in a position relative to the surgical distractor.

4. A surgical instrument as recited in claim 3, wherein the height controller is selectively fixable in the position via friction engagement with the surgical distractor.

5. A surgical instrument as recited in claim 1, wherein the first arm defines an axis and the height controller extends transverse to the axis.

6. A surgical instrument as recited in claim 1, wherein the first member is releasably engageable with the height controller via a mating connection.

7. A surgical instrument as recited in claim 1, wherein the first member is releasably engageable with the height controller via a snap fit connection.

8. A surgical instrument as recited in claim 1, wherein the first arm defines an axis and a first blade is rotatable about the axis.

9. A surgical instrument as recited in claim 8, further comprising a handle connected with the first member for rotating the first blade about the axis.

10. A surgical instrument as recited in claim 8, wherein:
the arm is a first arm, the axis is a first axis, and the second member includes a second arm defining a second axis; and
a second blade is rotatable about the second axis.

11. A surgical instrument as recited in claim 10, wherein the members include a lock, to selectively fix the first blade relative to the second blade, or a ratchet.

12. A surgical system comprising:
a first implant support and a second implant support, the implant supports being engaged with bone fasteners fixed with vertebral tissue;
a surgical distractor engageable with the implant supports, the surgical distractor including a projection;
a surgical retractor having a first member including a mating surface connectable with a first blade and a second member including a second blade and being movable relative to the first member such that the blades are movable to space tissue adjacent a spine, the surgical retractor comprising a ratchet extending through the first member and connected to the second member; and
a height controller including longitudinal rails that define a groove, the groove being configured for disposal of the projection such that the projection is slidably translatable within the groove, the height controller being connectable with the first member,
wherein the height controller is configured to adjust the height of the surgical retractor relative to the surgical distractor.

13. A surgical system as recited in claim 12, further comprising a stability element disposed with the implant supports and being alternately engageable with the first blade or the second blade.

14. A surgical system as recited in claim 13, wherein the implant supports define rod slots configured for slidable translation of the stability element.

15. A surgical system as recited in claim 13, wherein the stability element includes at least one mating pin being alternately engageable with the first blade or the second blade.

16. A surgical system comprising:
a first implant support and a second implant support, the implant supports being engaged with bone fasteners fixed with vertebral tissue, the first implant support defining a first rod slot and the second implant support defining a second rod slot;
a surgical retractor engageable with the implant supports, and including a first blade and a second blade; and
a stability element comprising opposite first and second end surfaces, the first end surface being disposed in the first rod slot and the second end surface being disposed in the second rod slot, the stability element comprising a section between the end surfaces, the section being coupled directly to one of the blades.

17. A surgical system as recited in claim 16, wherein the rod slots are configured for slidable translation of the stability element.

18. A surgical system as recited in claim 16, wherein the surgical retractor has a first member including a mating surface being alternately connectable with the first blade and a height controller, the height controller being connectable with a surgical distractor and configured to translate the first member relative to the surgical distractor, the surgical retractor further having a second member including the second blade and being movable relative to the first member such that the blades are movable to space tissue adjacent a spine.

19. A surgical system as recited in claim 18, wherein the height controller is selectively fixable in a position relative to the surgical distractor.

20. A surgical instrument as recited in claim 1, further comprising a ratchet extending through the first member and connected to the second member.

* * * * *